(12) United States Patent
Yen et al.

(10) Patent No.: US 11,896,340 B2
(45) Date of Patent: Feb. 13, 2024

(54) ROBOT NAVIGATION SYSTEM AND ROBOT NAVIGATION METHOD

(71) Applicant: NATIONAL TAIWAN UNIVERSITY, Taipei (TW)

(72) Inventors: Ping-Lang Yen, Taipei (TW); Tsung-Han Ho, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 522 days.

(21) Appl. No.: 17/093,660

(22) Filed: Nov. 10, 2020

(65) Prior Publication Data
US 2021/0137623 A1 May 13, 2021

Related U.S. Application Data

(60) Provisional application No. 62/933,988, filed on Nov. 12, 2019.

(51) Int. Cl.
*A61B 34/00* (2016.01)
*A61B 34/20* (2016.01)
(Continued)

(52) U.S. Cl.
CPC .............. *A61B 34/74* (2016.02); *A61B 34/20* (2016.02); *A61B 34/37* (2016.02); *A61B 90/37* (2016.02);
(Continued)

(58) Field of Classification Search
CPC ......... A61B 34/10; A61B 34/30; A61B 34/20; A61B 90/39; A61B 2090/364;
(Continued)

(56) References Cited

U.S. PATENT DOCUMENTS

| | | | |
|---|---|---|---|
| 10,279,154 B2 | 5/2019 | Heilman et al. | |
| 10,350,372 B2 | 7/2019 | Centeno et al. | |
| 2016/0354162 A1* | 12/2016 | Yen | A61B 34/20 |

FOREIGN PATENT DOCUMENTS

| | | |
|---|---|---|
| CN | 106963490 B | 11/2019 |
| CN | 209574879 U | 11/2019 |
| TW | 201924612 A | 7/2019 |

OTHER PUBLICATIONS

Wagner, A., Nübel, M., Badreddin, E., Pott, P., & Schwarz, M. L. (2007). Disturbance feed forward control of a handheld parallel robot. In ICINCO-RA (1) (pp. 44-51). (Year: 2007).*
(Continued)

*Primary Examiner* — Keith M Raymond
*Assistant Examiner* — Johnathan Maynard
(74) *Attorney, Agent, or Firm* — CKC & Partners Co., LLC

(57) ABSTRACT

A robot navigation system includes a handheld robot, a spatial information measuring device, a computing module and a display. The hand-held robot has a body, a tool and a movable connection mechanism. The movable connection mechanism is connected between the body and the tool, so that the tool can move relative to the body. The spatial information measuring device is configured to track the body, the tool and a target. The computing module is connected to the spatial information measuring device to obtain a plurality of relative positions between the body, the tool and the movable connection mechanism with respect to the target. The computing module calculates a guiding region according to the relative positions and mechanical parameters of the handheld robot. The display is configured to display the guiding region and the handheld robot based on the coordinate of the target.

5 Claims, 14 Drawing Sheets

(51) Int. Cl.
 A61B 34/37 (2016.01)
 A61B 90/00 (2016.01)
(52) U.S. Cl.
 CPC ...... *A61B 90/39* (2016.02); *A61B 2034/2048* (2016.02); *A61B 2034/2051* (2016.02); *A61B 2034/2068* (2016.02); *A61B 2090/372* (2016.02); *A61B 2090/3983* (2016.02)
(58) Field of Classification Search
 CPC ........ A61B 2090/365; A61B 2090/367; A61B 2090/368; A61B 2090/371; A61B 2090/373; A61B 2090/3904; A61B 2090/3908; A61B 2090/3912; A61B 2090/3916; A61B 2090/3929; A61B 2090/3937; A61B 2090/3945; A61B 2090/3958; A61B 2090/3983; A61B 2090/3975; A61B 2090/3979; A61B 5/06; A61B 5/061; A61B 5/064; A61B 5/065; A61B 5/066; A61B 2034/2046; A61B 2034/2055; A61B 2034/301; A61B 2034/302; A61B 2034/303; A61B 2034/101; A61B 2034/102; A61B 2034/103; A61B 2034/104; A61B 2034/105; A61B 2034/106; A61B 2034/107; A61B 2034/108; A61B 90/37
 See application file for complete search history.

(56) References Cited

OTHER PUBLICATIONS

Pott, P. P., Hessinger, M., Werthschützky, R., Schlaak, H. F., Nordheimer, E., Badreddin, E., & Wagner, A. Active Surgeon Support during Orthopedic Surgery using the BOrESCOPE-Exoskeleton: System Design and First Results. International Journal on Advances in Life Sciences, 6(3-4). (Year: 2014).*
Yen, P. L., Wang, C. H., Lin, H. T., & Hung, S. S. (2019). Optimization design for a compact redundant hybrid parallel kinematic machine. Robotics and Computer-Integrated Manufacturing, 58, 172-180. (Year: 2019).*
Kelly, R. (1996). Robust asymptotically stable visual servoing of planar robots. IEEE Transactions on Robotics and Automation, 12(5), 759-766. (Year: 1996).*
Robert D. Howe, et al., "Robotics for Surgery", Annual Review of Biomedical Engineering, 1999, vol. 1, pp. 211-240, Annual Reviews, United States.
Christos Bergeles, et al., "From passive tool holders to microsurgeons: safer, smaller, smarter surgical robots", IEEE Transactions on Biomedical Engineering, May 2014, vol. 61, No. 5, pp. 1565-1576, IEEE, United States.
Russell H. Taylor, et al., "Medical Robotics and Computer-Integrated Surgery", Springer Handbook of Robotics, 2016, pp. 1657-1684, Springer, Germany.
Ferdinando Rodriguez y Baena, et al., "Robotic Surgery: From Autonomous Systems to Intelligent Tools", Robotica, 2010, vol. 28, No. 2, pp. 163-170, Cambridge University Press, United Kingdom.
Hyung L. Kim, et al., "The Paky, Hermes, Aesop, Zeus, and da Vinci robotic systems", Urologic Clinics of North America, 2004, vol. 31, No. 4, pp. 659-669, Elsevier, Netherlands.
Lee J. Moore, et al., "Robotic technology results in faster and more robust surgical skill acquisition than traditional aparoscopy", Journal of Robotic Surgery, 2015, vol. 9, pp. 67-73, Springer, Germany.
Jan Persson, et al., "Reproducibility and accuracy of robot-assisted laparoscopic fertility sparing radical rachelectomy", Gynecologic Oncology, 2012, vol. 127, pp. 484-488, Elsevier, Netherlands.
Gabriel I. Barbash, et al., "New Technology and Health Care Costs—The Case of Robot-Assisted Surgery", The New England Journal of Medicine, Aug. 19, 2010, vol. 363, pp. 701-704, Massachusetts Medical Society, United States.
Jad Khoraki, et al., "Perioperative outcomes and cost of robotic-assisted versus laparoscopic inguinal hernia repair", Surgical Endoscopy, 2020, vol. 34, pp. 3496-3507, Springer, Germany.
Michel Lefranc, et al., "Evaluation of the ROSA™ Spine robot for minimally invasive surgical procedures", Expert Review of Medical Devices, 2016, vol. 13, No. 10, pp. 899-906, Informa, United Kingdom.
Michel Lefranc, et al., "Frameless robotic stereotactic biopsies: a consecutive series of 100 cases", Journal of Neurosurgery, Feb. 2015, vol. 122, pp. 342-352, American Association of Neurological Surgeons, United States.
Wei Tian, et al., "Robot-assisted Anterior Odontoid Screw Fixation: A Case Report", Orthopaedic Surgery, 2016, vol. 8, No. 3, pp. 400-404, Chinese Orthopaedic Association, China and John Wiley & Sons Australia, Ltd, Australia.
Brian L. Davies, et al., "Hands-On Robotic Surgery: Is This the Future?", Medical Imaging and Augmented Reality, 2004, pp. 27-37, Springer-Verlag Berlin Heidelberg, Germany.
Benny Hagag, et al., "RIO: Robotic-Arm Interactive Orthopedic System MAKOplasty: User Interactive Haptic Orthopedic Robotics", Surgical Robotics, 2011, Springer Science+Business Media, LLC, Germany.
Russell Taylor, et al., "A Steady-Hand Robotic System for Microsurgical Augmentation", The International Journal of Robotics Research, Dec. 1999, vol. 18, No. 12, pp. 1201-1210, Sage Publications, Inc., United States.
Martin Roche, "Robotic-assisted Unicompartmental Knee Arthroplasty: The MAKO Experience", Clinics in Sports Medicine, Jan. 2014, vol. 33, No. 1, pp. 123-132, Elsevier, Netherlands.
Rupesh Tarwala, et al., "Robotic assisted total hip arthroplasty using the MAKO platform", Current Reviews in Musculoskeletal Medicine, 2011, vol. 4, No. 151, pp. 151-156, Springer, Germany.
Frederic Picard, et al., "Computer assisted orthopaedic surgery: Past, present and future", Medical Engineering and Physics, 2019, vol. 72, pp. 55-65, Elsevier, Netherlands.
Christopher J. Payne, et al., "Hand-Held Medical Robots", Annals of Biomedical Engineering, Aug. 2014, vol. 42, No. 3, pp. 1594-1605, Springer Science+Business Media, United States.
Sungwook Yang, et al., "Manipulator Design and Operation of a Six-Degree-of-Freedom Handheld Tremor-Canceling Microsurgical Instrument", IEEE/ASME Transactions on Mechatronics, Apr. 2015, vol. 20, No. 2, pp. 761-772, IEEE, United States.
Cameron N. Riviere, et al., "Toward active tremor canceling in handheld microsurgical instruments", IEEE Transactions on Robotics and Automation, 2003, vol. 19, No. 5, pp. 793-800, IEEE, United States.
Daniel E. Whitney, "Resolved Motion Rate Control of Manipulators and Human Prostheses," IEEE Transactions on Man-Machine Systems, Jan. 1969, vol. MMS-10, No. 2, pp. 47-53, IEEE, United States.
Ping-Lang Yen, et al., "Optimization design for a compact redundant hybrid parallel kinematic machine," Robotics and Computer Integrated Manufacturing, 2019, vol. 58, pp. 172-180, Elsevier, Netherlands.
T. B. Sheridan, "Telerobotics, Automation and Human Supervisory Control", 1992, pp. 65, MIT Press, United States.
Toshiyuki Inagaki, "Adaptive automation: Sharing and Trading of Control", Chapter 8 of the Handbook of Cognitive Task Design, 2003, pp. 147-169, Lawrence Erlbaum Associates, Inc., United States.
Paul G. Griffiths, et al., "Sharing Control Between Humans and Automation Using Haptic Interface: Primary and Secondary Task Performance Benefits", Human factors, 2005, vol. 47, No. 3, pp. 574-590, Human Factors and Ergonomics Society, United States.
Samad Hayati, et al., "Design and implementation of a robot control system with traded and shared control capability", Proceedings, 1989 International Conference on Robotics and Automation, pp. 1310-1315, IEEE, United States.
Ahmet Emre Cetin, et al., "Cooperative control of a human and a robot manipulator for positioning a cart on a frictionless plane", Mechatronics, 2006, vol. 16, pp. 461-469, Elsevier, Netherlands.

(56) References Cited

OTHER PUBLICATIONS

Ahmet Emre Cetin, et al., "Implementation and Development of an Adaptive Steering-Control System", IEEE Transactions on Vehicular Technology, Jan. 2010, vol. 59, No. 1, pp. 75-83, IEEE, United States.

Anthony M. Digioia, et al., "Computer Assisted Orthopaedic Surgery: Image Guided and Robotic Assistive Technologies", Clinical Orthopaedics and Related Research, 1998, vol. 354, pp. 8-16, Lippincott Williams & Wilkins, Inc., United States.

Clément M. Gosselin, et al., "Singularity analysis of closed-loop kinematic chains", IEEE Transactions on Robotics and Automation, Jul. 1990, vol. 6, No. 3, pp. 281-290, IEEE, United States.

Stephen L. Chiu, "Task Compatibility of Manipulator Postures", The International Journal of Robotics Research, Oct. 1988, vol. 7, No. 5, pp. 13-21, Sage Publications, United States.

Tamas Ungi et al., "Open-source platforms for navigated image-guided interventions", Medical Image Analysis, 2016, vol. 33, pp. 181-186, Elsevier, Netherlands.

Ping-Lang Yen et al., "Navigation Graphics to Coordinate the Human and Robot Behavior for Handheld Robot Positioning", 2019 IEEE/ASME International Conference on Advanced Intelligent Mechatronics, Jul. 8-12, 2019, pp. 98-102, IEEE, Hong Kong.

Frank Bova, "Computer Based Guidance in the Modern Operating Room: A Historical Perspective", IEEE Reviews in Biomedical Engineering, 2010, vol. 3, pp. 209-222, IEEE, United States.

M. E. Allaf, et al., "Laparoscopic visual field Voice vs foot pedal interfaces for control of the Aesop robot", Surgical Endoscopy, 1998, vol. 12, No. 12, pp. 1415-1418, Springer, United States.

Ian K. McLeod, et al., "Potential applications of the da Vinci minimally invasive surgical robotic system in btolaryngology", Ear, Nose & Throat Journal, Aug. 2005, vol. 84, No. 8, pp. 483-487, Sage Publications, United States.

Nabil Simaan, et al., "Design and Integration of a Telerobotic System for Minimally Invasive Surgery of the Throat", The International Journal of Robotics Research, Nov. 2009, vol. 29, pp. 1661-1683, MIT Press, United States.

M Jakopec, et al., "The First Clinical Application of a "Hand'S On" Robotic Knee Surgery System", Computer Aided Surgery, 2001, vol. 6, pp. 329-339, John Wiley & Sons, England.

* cited by examiner

ROBOT NAVIGATION SYSTEM AND ROBOT NAVIGATION METHOD

RELATED APPLICATIONS

This application claims priority to US Provisional Application Ser. No. 62/933,988, filed Nov. 12, 2019, which is herein incorporated by reference in its entirety.

BACKGROUND

Field of Disclosure

The present disclosure relates to a robot navigation system and a robot navigation method, particularly for handheld robots.

Description of Related Art

The handheld robot for surgery occupies a small space in the operating room. The operation of the handheld robot is also convenient to directly provide immediate feel of tool tip's force to the operator's hand. During the operation, all procedures can be completed jointly by the operator and the handheld robot.

The operator and the handheld robot affect each other. However, when the human-machine collaboration relationship between the operator and the handheld robot is poor, the handheld robot can deviate from the target and exceed the working space, and the operator would also obviously feel the reaction force generated during the compensation process, resulting in the inaccuracy of the overall operation with reduced fluency.

SUMMARY

An aspect of the present disclosure is related to a robot navigation system.

According to one or more embodiments of the present disclosure, a robot navigation system includes a handheld robot, a spatial information measuring device, a computing module and a display. The handheld robot has a body, a tool and a movable connection mechanism connected to each other. The movable connection mechanism is connected between the body and the tool such that the tool is movable relative to the body. The spatial information measuring device is configured to track the body, the tool and a target. The computing module is connected to the spatial information measuring device to obtain a plurality of relative positions of the body, the tool and the movable connection mechanism with respect to the target. The computing module is configured to calculate a guiding region according to the relative positions and mechanical parameters of the handheld robot. The display is configured to display the guiding region and the handheld robot with respect to the coordinate system of the target.

In one or more embodiments of the present disclosure, the handheld robot further includes a controller electrically connected to the movable connection mechanism and configured to adjust the relative position and an orientation of the tool with respect to the target. The controller is connected to the computing module, and the controller is configured to adjust a spin angle of the movable connection mechanism to maximize the guiding region displayed by the display.

In some embodiments of the present disclosure, the spatial information measuring device includes an optical tracker, a first optical marker located on the body, a second optical marker located on the tool and a third optical marker located on the target. The optical tracker obtains the relative positions of the body and the tool with respect to the target through the first optical marker, the second optical marker and the third optical marker.

In some embodiments of the present disclosure, the spatial information measuring device includes a receiving and transmitting device, a first magnetic field coil located on the body, a second magnetic field coil located on the tool and a third magnetic field coil located on the target. The receiving and transmitting device is configured to obtain the relative positions of the body and the tool with respect to the target through the first magnetic field coil, the second magnetic field coil and the third magnetic field coil.

In some embodiments of the present disclosure, the spatial information measuring device includes a first inertial measurement unit located on the body, a second inertial measurement unit located on the tool and a third inertial measurement unit located on the target. The relative positions of the body, the tool with respect to the target are obtained by the first inertial measurement unit, the second inertial measurement unit and the third inertial measurement unit.

In some embodiments of the present disclosure, the spatial information measuring device includes any combinations of the optical, magnetic and inertial measuring devices.

In one or more embodiments of the present disclosure, the spatial information measuring device includes a first measuring device, a second measuring device and a third measuring device. The first measuring device is located on the body. The first measuring device includes one of a first optical marker, a first magnetic field coil and a first inertial measurement unit. The second measuring device is located on the tool. The second measuring device includes one of a second optical marker, a second magnetic field coil and a second inertial measurement unit. The third measuring device is located on the target. The third measuring device includes one of a third optical marker, a third magnetic field coil and a third inertial measurement unit.

In one or more embodiments of the present disclosure, the display is located on the body of the handheld robot.

In one or more embodiments of the present disclosure, the computing module is configured to calculate two relative speeds of the body and the tool with respect to the target according to the relative positions. An optimal operation plane is selected by the computing module according to the mechanical parameters, and the computing module is further configured to locate the guiding region on the optimal operation plane according to the relative positions, the two relative speeds, and the mechanical parameters.

An aspect of the present disclosure is related to a robot navigation method.

According to one or more embodiments of the present disclosure, a robot navigation method includes following operations. A body, a tool and a target of a handheld robot is tracked to obtain a plurality of relative positions of the body, the tool, and a movable connection mechanism connecting the body and the tool with respect to the target. A guiding region based on a coordinate of the target is calculated. The operation of calculating a guiding region based on a coordinate of the target includes following operations. Calculating two relative speeds of the movable connection mechanism and the tool with respect to the target according to the relative positions. Calculating the guiding region according to the relative positions and the two relative speeds of the handheld robot. The target, the guiding region and the handheld robot are displayed on a display based on the coordinate of the target.

In one or more embodiments of the present disclosure, operation of calculating the guiding region based on the coordinate of the target further includes following operation. An optimal operation plane is selected according to the mechanical parameters. The guiding region is located on the optimal operation plane.

In one or more embodiments of the present disclosure, mechanical parameters of the handheld robot include a position error of the movable connection mechanism. Operation of calculating the guiding region based on the coordinate of the target further includes following operations. Establishing a coordinate conversion relation between the movable connection mechanism and the tool. Calculating a kinetic energy of the tool through the coordinate conversion relation, the kinetic energy is related to the two relative positions of the movable connection mechanism and the tool with respect to the target. Limiting a range of the kinetic energy of the tool by a kinetic energy of the movable connection mechanism and the position error, and the guiding region is defined by the range of the kinetic energy of the tool.

In one or more embodiments of the present disclosure, operation of calculating the guiding region based on the coordinate of the target further includes following operation. The spin angle of the movable connection mechanism is adjusted to maximize the guiding region displayed by the display.

In some embodiments of the present disclosure, operation of displaying the target, the guiding region and the handheld robot on the display based on the coordinate of the target further includes following operation. Rotating the body to minimize an orientation error of the tool with respect to the target. The handheld robot displayed on the display comprises the body and the tool, an area of a representation corresponding to the body is minimized when the relative spin angle is minimized.

In one or more embodiments of the present disclosure, operation of displaying the target, the guiding region and the handheld robot on the display based on the coordinate of the target further includes following operations. Rotating the body to minimize an orientation error of the tool with respect to the target. The handheld robot displayed on the display comprises the body and the tool, a thickness of a representation corresponding to the body is minimized when the orientation error is minimized.

In summary, the present disclosure provides a robot navigation system and a corresponding robot navigation method. When an operator operates a handheld robot, the robot navigation method can incorporate human into the control loop. Through the relevant navigation visual interface, the operator is dynamically and intuitively guided to move and operate the handheld robot. Therefore, for example, the tremor caused by the hand's involuntary motion of the operator can be suppressed by the mentioned robot navigation method.

It is to be understood that both the foregoing general description and the following detailed description are by examples, and are intended to provide further explanation of the invention as claimed.

BRIEF DESCRIPTION OF THE DRAWINGS

The advantages of the present disclosure are to be understood by the following exemplary embodiments and with reference to the attached drawings. The illustrations of the drawings are merely exemplary embodiments and are not to be considered as limiting the scope of the present disclosure.

DETAILED DESCRIPTION

The following embodiments are disclosed with accompanying diagrams for detailed description. For illustration clarity, many details of practice are explained in the following descriptions. However, it should be understood that these details of practice do not intend to limit the present invention. That is, these details of practice are not necessary in parts of embodiments of the present invention. Furthermore, for simplifying the drawings, some of the conventional structures and elements are shown with schematic illustrations. Also, the same labels may be regarded as the corresponding components in the different drawings unless otherwise indicated. The drawings are drawn to clearly illustrate the connection between the various components in the embodiments, and are not intended to depict the actual sizes of the components.

In addition, terms used in the specification and the claims generally have the usual meaning as each terms are used in the field, in the context of the disclosure and in the context of the particular content unless particularly specified. Some terms used to describe the disclosure are to be discussed below or elsewhere in the specification to provide additional guidance related to the description of the disclosure to specialists in the art.

The phrases "first," "second," etc., are solely used to separate the descriptions of elements or operations with the same technical terms, and are not intended to convey a meaning of order or to limit the disclosure.

Additionally, the phrases "comprising," "includes," "provided," and the like, are all open-ended terms, i.e., meaning including but not limited to.

Further, as used herein, "a" and "the" can generally refer to one or more unless the context particularly specifies otherwise. It will be further understood that the phrases "comprising," "includes," "provided," and the like used herein indicate the stated characterization, region, integer, step, operation, element and/or component, and does not exclude additional one or more other characterizations, regions, integers, steps, operations, elements, components and/or groups thereof.

To solve the problem of inaccurate operation caused by the mutual influence between the operator and the robot (e.g., surgical robot, etc.) in human-machine cooperation, the present disclosure provides a robot navigation system and a robot navigation method that can simplify and clearly remind the operator how to control the mobile robot to suppress uncontrollable factors caused by the reaction force of human-machine interaction.

Figure 1:
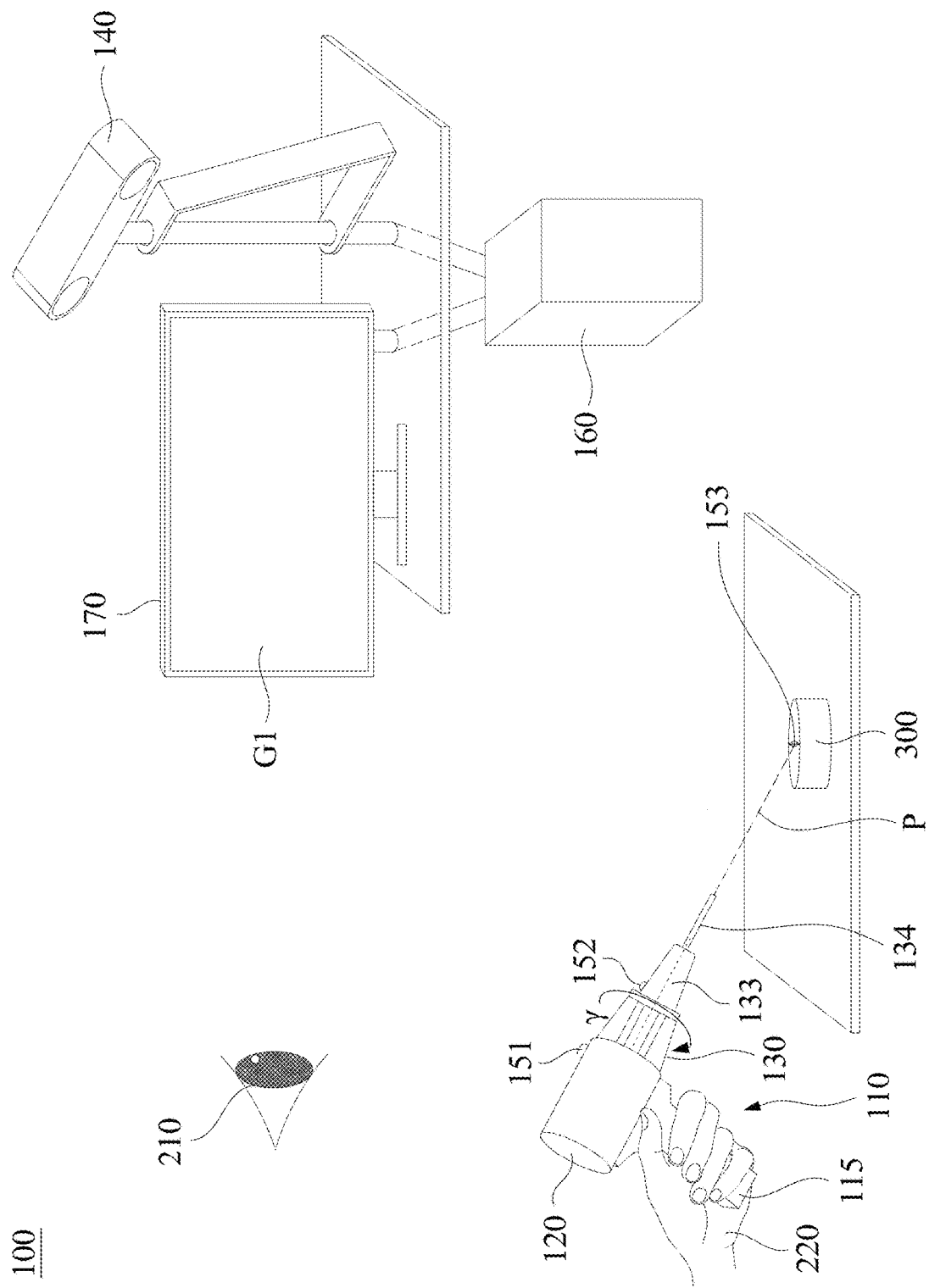
FIG. 1 illustrates a schematic view of a robot navigation system according to an embodiment of the present disclosure.

Reference is made by FIG. 1. FIG. 1 illustrates a schematic view of a robot navigation system 100 according to an embodiment of the present disclosure;

In this present embodiment, the robot navigation system 100 is used, for example, in orthopedic surgery to install supporting equipment in a target in the human body. For the purpose of simple description, in FIG. 1, the operator operates the handheld robot 110 to move and the target 300 is schematically drawn.

As shown in FIG. 1, in this embodiment, the robot navigation system 100 includes a handheld robot 110, a spatial information measuring device, a computing module 160 and a display 170. The computing module 160 is connected to the display 170 and the optical tracker 140.

In this embodiment, the spatial information measuring device includes an optical tracker 140, an optical marker 151, an optical marker 152 and an optical marker 153. The optical tracker 140 can tracking the optical marker 151, the optical marker 152, and the optical marker 153 to perform a positioning function. However, this disclosure does not limit the types of spatial information measuring devices by this embodiment.

In some embodiments, the computing module 160 includes devices such as a micro controller unit, a processor, a mobile device, a computer or a server, so as to implement data processing and computing functions. In some embodiments, the computing module 160 can be remotely connected to the handheld robot 110. For example, the computing module 160 can be connected to the handheld robot 110 via a Bluetooth or wireless network.

A hand 220 of the operator holds the handheld robot 110, and sight 210 of the operator looks at the display 170. Therefore, the operator can operate the handheld robot 110 to approach the target 300 according to the medical image and the navigation image G1 displayed on the display interface of the display 170.

As shown in FIG. 1, in this embodiment, the handheld robot 110 includes a handle 115, a body 120, a movable connection mechanism 130 and a tool 133. The hand 220 of the operator holds the handheld robot 110 through the handle 115. The tool 133 that can be used to set the equipment to the human body is connected to the body 120 through the movable connection mechanism 130.

For example, in some embodiments of the present disclosure, as shown in FIG. 1, the tool 133 includes a tip 134. The tip 134 of the tool 133 can be used to lock a supporting equipment to the target 300. The movable connection mechanism 130 can finely adjust the position and the orientation of the tip 134 of the tool 133. In other words, the movable connection mechanism 130 can be regarded as the actuators used for fine-tuning the tool 133.

As shown in FIG. 1, in this embodiment, a spin angle of the movable connection mechanism 130 can be defined an angle γ rotated about the axis of the tip 134 of the tool 133.

Figure 2A:
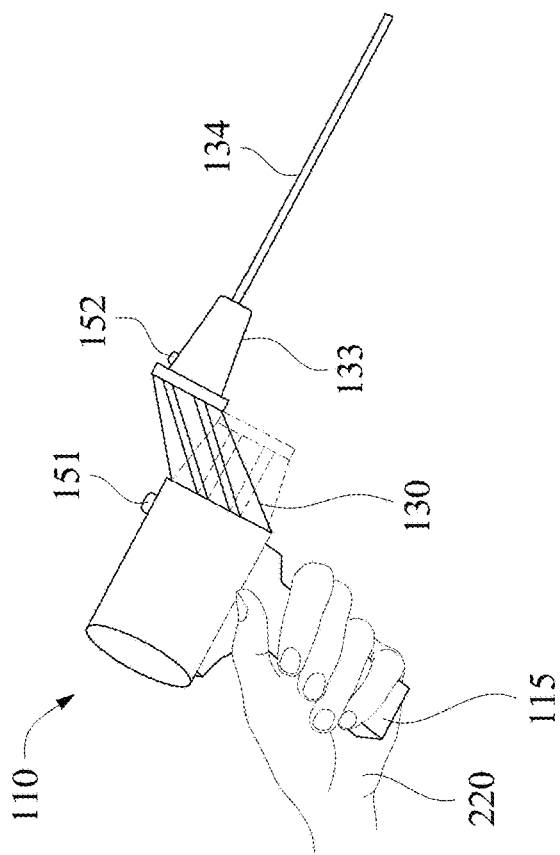
FIGS. 2A and 2B illustrate schematic views of a tool on a handheld robot moving through a movable connection mechanism according to an embodiment of the present disclosure.
Figure 2B:
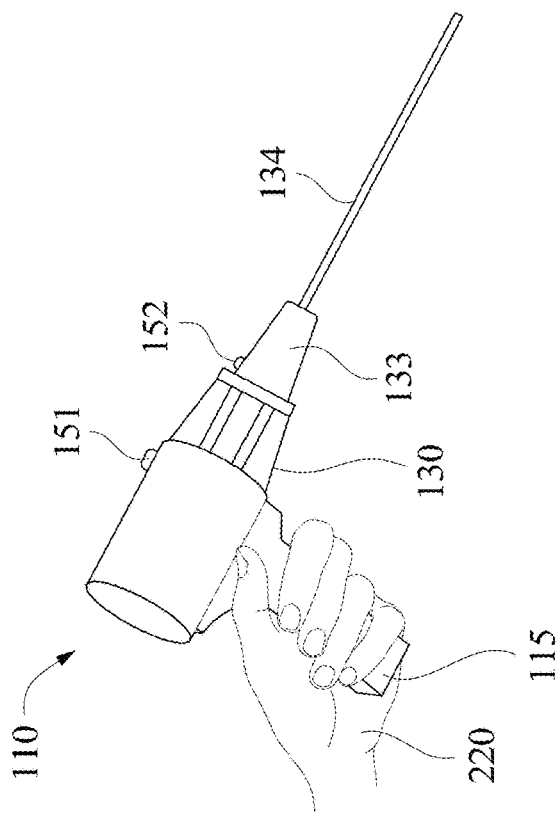

Reference is made by FIGS. 2A and 2B. FIGS. 2A and 2B illustrate schematic views of a tool 133 on a handheld robot 110 moving through the movable connection mechanism 130 according to an embodiment of the present disclosure.

In FIG. 2A, the movable connection mechanism 130 of the hand-held robot 110 is not offset, which is the standard case of the handheld robot 110. It corresponds to that the handheld robot 110 has been aligned with the target 300 at an appropriate orientation, so the movable connection mechanism 130 does not need to work.

In FIG. 2B, the hand 220 of the operator moves the handheld robot 110 through the handle 115. At this time, in order to align the tip 134 of the tool 133 with the target 300, the movable connection mechanism 130 would depart from its original position. For example, in some embodiments, the movable connection mechanism 130 is a six-axis robotic arm, and the six robotic arms of the handheld robot 110 can each perform a certain degree of angular offset and expansion in different axial directions, so that the tool 133 moves and the tip 134 of the tool 133 is aligned with the target 300.

Figure 3:
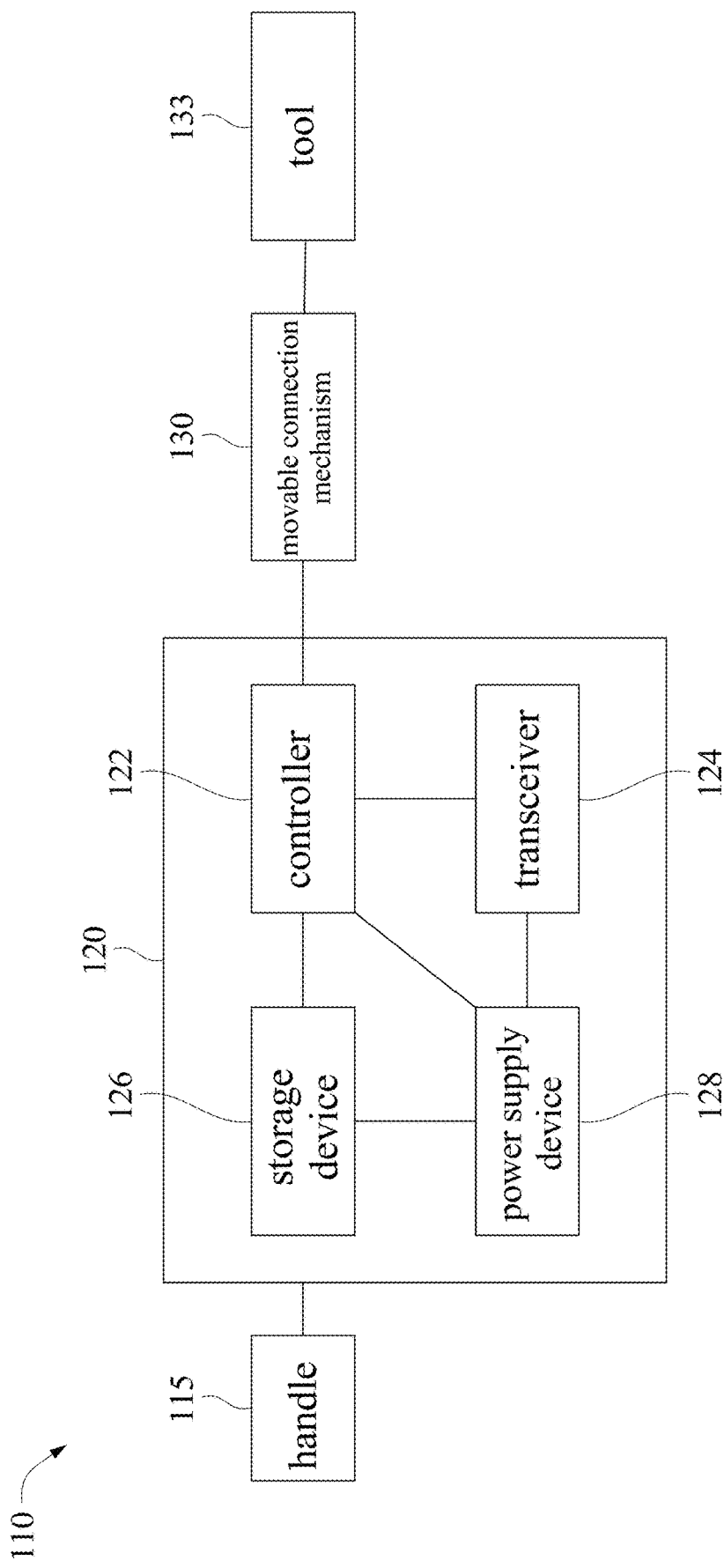
FIG. 3 illustrates a block diagram of a handheld robot according to an embodiment of the present disclosure.

To further discuss the composition of the handheld robot 110, please refer to FIG. 3. FIG. 3 illustrates a block diagram of a handheld robot 110 according to an embodiment of the present disclosure.

As shown in FIG. 3, in some embodiments of the present disclosure, the handheld robot 110 has a handle 115, a body 120, a movable connection mechanism 130 and a tool 133. The handle 115 is fixed to the body 120, so there is no relative movement between the handle 115 and the body 120.

In some embodiments of the present disclosure, the body 120 of the handheld robot 110 includes a controller 122, a transceiver 124, a storage device 126 and a power supply device 128. The power supply device 128 is connected to the controller 122, the transceiver device 124 and the storage device 126 to provide power required for operation.

In FIG. 3, the controller 122 is connected to the movable connection mechanism 130, so as to control the movable connection mechanism 130 to move the tool 133 to maintain that the tip 134 is aligned with target 300. The storage device 126 is connected to the controller 122 and can be used to store mechanical parameters of the handheld robot 110 and can record the movement data of the movable connection mechanism 130.

For example, in some embodiments, the movable connection mechanism 130 is six-axis robotic arms. Once the controller 122 adjusts the six-axis robot arm of the movable connection mechanism 130, the controller 122 can vary the position of each robotic arm relative to the body 120 and store the data of these positions in the storage device 126.

In the body 120 of the handheld robot 110 shown in FIG. 3, the transceiver 124 is connected to the controller 122. The transceiver 124 is used to transmit the data stored in the storage device 126 to the computing module 160 (as shown in FIG. 1). The transceiver 124 can also remotely receive the signal sent by the computing module 160. After the computing module 160 receives the data from the handheld robot 110, it can calculate a control signal suitable for controlling the movable connection mechanism 130 through an algorithm. For details, please refer to the following discussion. The transceiver 124 can then receive the control signal from the computing module 160 to enable the controller 122 to adjust the movable connection mechanism 130 to set the position of the tool 133.

Therefore, the tool 133 of the handheld robot 110 can adjust the position adaptively following the target 300.

Return to FIG. 1. In this embodiment, the optical tracker 140 is used to track the handheld robot 110. More specifically, in this embodiment, the optical tracker 140 tracks the body 120 of the handheld robot 110, the tool 133 and the target 300.

As shown in FIG. 1, in this embodiment, the spatial measuring device of the robot navigation system 100 includes an optical tracker 140, an optical marker 151, an optical marker 152 and an optical marker 153. The optical marker 151 is located on the body 120. The optical marker 152 is located on the tool 133. The optical marker 153 is located on the target 300. Therefore, the optical tracker 140 can track the optical marker 151, the optical marker 152, and the optical marker 153 to position the body 120 and the tool 133 of the handheld robot 110 and target 300 through the optical marker 151, the optical marker 152, and the optical marker 153, respectively.

It should be noted that FIG. 1 only schematically indicates the positions in which the optical marker 151, the optical marker 152 and the optical marker 153 are located but not limit the structure or aspect of the optical marker 151, the optical marker 152, and the optical marker 153. In some embodiments, in order to achieve a more precise positioning effect, the optical marker 151, the optical marker 152, and the optical marker 153 can respectively be devices that integrate multiple sub-optical marks. For example, in some embodiments, to obtain the position of the moving tool 133 more accurately, the optical marker 153 can integrate four or more sub-optical marker devices. The positions of these sub-optical marks can extend from the body 120 to the tip 134 of the tool 133 but is not limited to the present disclosure.

The calculation module 160 is connected to the optical tracker 140. Through the optical marker 151, the optical marker 152 and the optical marker 153, the optical tracker 140 can track and position the body 120 of the handheld robot 110, the tool 133 and the target 300. The optical tracker 140 transmits the positioning data to the calculation module 160, and the computing module 160 can obtain the relative positions of the body 120 and the tool 133 of the handheld robot 110 with respect to the target 300.

As mentioned above, in the present disclosure, the optical tracker 140, the optical marker 151, the optical marker 152 and the optical marker 153 of this embodiment are not used to limit the types of the spatial information measuring device of the present disclosure. In some embodiments, the optical tracker 140 in FIG. 1 can be replaced with a magnetic field transmitting and receiving device, and the optical marker 151, the optical marker 152 and the optical marker 153 can be replaced with three magnetic field coils, respectively. That is, the three magnetic field coils are respectively installed on the body, the tool, and the target, replacing the original positions of the optical marker 151, the optical marker 152, and the optical marker 153 in FIG. 1. In this way, the magnetic field transmitting and receiving device can transmit or receive electromagnetic signals by which three magnetic field coils are respectively arranged on the body 120, the tool 133 and the target 300 to position the body 120, the tool 133 and the target 300, thereby obtaining the relative positions of the body 120 and the tool 133 of the handheld robot 110 through the computing module 160.

In some embodiments, the spatial information measurement device can also use an inertial measurement unit. The inertial measurement unit can obtain the velocity and angular acceleration of the object to be measured. Given the initial conditions, it would be possible to obtain the location and attitude changes of the object to be measured (that is, relative rotation in different axes relative to the initial position) by inertial navigation, without the need for additional trackers. For example, in an embodiment using an inertial measurement unit as a spatial information measurement device, the optical tracker 140 in FIG. 1 can be removed, and the optical marker 151, the optical marker 152 and the optical marker 153 can be replaced with three inertial measurement units respectively. That is, the three inertial measurement units are installed on the body 120, the tool 133 and the target 300 respectively, replacing the three optical marks 151, 152 and 153 located on the original positions in FIG. 1. In this case, the three inertial measurement units are remotely connected to the computing module 160. After the handheld robot 110 starts to move, the three inertial measurement units can locate the body, the tool, and the target based on the initial conditions, and then obtain the relative positions of the body 120 and the tool 133 of the handheld robot 110 with respect to the target 300 through the computing module 160.

In some embodiments of the present disclosure, the spatial information measuring device includes any combinations of the optical, magnetic and inertial measuring devices. Specifically, in one or more embodiments of the present disclosure, the spatial information measuring device includes a first measuring device located on the body, a second measuring device located on the tool and a third measuring device on the target. Each of the first measuring device, the second measuring device and the third measuring device includes one of an optical marker, a magnetic measuring device (e.g. magnetic field coil) and an inertial measurement unit.

In some embodiments, the spatial information measuring device may also capture the image of the handheld robot 110 in real time and obtain the relative position of the body 120 and the tool 133 with respect to the target 300 through image analysis.

Furthermore, as mentioned above, the controller 122 and the storage device 126 in the body 120 of the handheld robot 110 can record the position data of the movable connection mechanism 130 relative to the body 120. Therefore, by remotely transmitting the position data of the movable connection mechanism 130 relative to the body 120 to the computing module 160, the computing module 160 can obtain the relative position of the movable connection mechanism 130 with respect to the target 300. For example, if the movable connection mechanism 130 includes six-axis robotic arms, the computing module 160 can obtain the relative positions of the six robotic arms with respect to the target 300.

Therefore, the computing module 160 can obtain the relative positions of the body 120, the movable connection mechanism 130 and the tool 133 of the handheld robot 110 with respect to the target 300. In addition, by recording the changes of the relative positions of the body 120, the movable connection mechanism 130 and the tool 133 of the handheld robot 110 with respect to the target 300 over time in real time, the computing module 160 can obtain the speed and kinetic energy of the body 120, the movable connection mechanism 130 and the tool 133.

The hand 220 of the operator holds the handle 115, and the handle 115 is fixed to the body 120. By recording the relative position and speed of the body 120, the computing module 160 can obtain the force exerted by the operator on the handheld robot 110 and also reflect the influence of the handheld robot 110 on reaction force to the operator.

The relative position and speed of the movable connection mechanism 130 reflect the real-time movement of the tool 133. At the same time, the movable connection mechanism 130 also has mechanical parameters, which also limits the range in which the tool 133 can move.

As shown in FIG. 1, the issue to be solved for the robot navigation system 100 is to guide the tip 134 of the tool 133 to the target 300 so that the tip 134 of the tool 133 can be installed on the target 300. The path P is between the tip 134 of the tool 133 and the target 300. The specifications of the movable connection mechanism 130 and the tool 133 of the handheld robot 110 are known. Therefore, after obtaining the relative positions of the body 120, the movable connection mechanism 130 and the tool 133 with respect to the target 300, the computing module 160 can calculate the path P of the tip 134 of the tool 133 with respect to the target 300.

Based on the above conditions, the computing module 160 can limit a better path P based on the relative position and speed of the body 120 the movable connection mechanism 130 and the tool 133 of the handheld robot 110 with respect to the target 300. The optimized path P and the target 300 can be presented on the display 170 as a medical image and a navigation image G1. Therefore, the operator can confirm the prompt of the medical image and the navigation image G1 on the display 170 with the sight 210 and move the handheld robot 110 with the hand 220 according to the prompt. In the process of moving the handheld robot 110, the optical tracker 140 can continuously track the body 120 and the tool 133 of the handheld robot 110 and present relevant information on the medical image and the navigation image G1 on the display 170.

It should be noted that FIG. 1 only schematically indicates the location of the medical image and the navigation image G1 for the purpose of simple description. The specific navigation method of the computing module 160 planning path P and the specific content of the medical image and the navigation image G1, please refer to the following discussion.

In some embodiments, the medical image and navigation image G1 also include other auxiliary information, such as real-time medical images or medical data. The medical image is, for example, a real-time image of the affected part of the operator. After the operator guides the handheld robot 110 to move and position through the medical image and the navigation image G1 provided by the display 170, the sight 210 of the operator can change the real-time medical image in the medical image and the navigation image G1 to perform the operation. In short, the display 170 connected to the computing module 160 displays medical images and navigation images G1 to guide the operator to move the handheld robot 110 in place. Subsequently, the operator performs the operation according to the medical image in the display 170 and the medical image in the navigation image G1.

Figure 4:
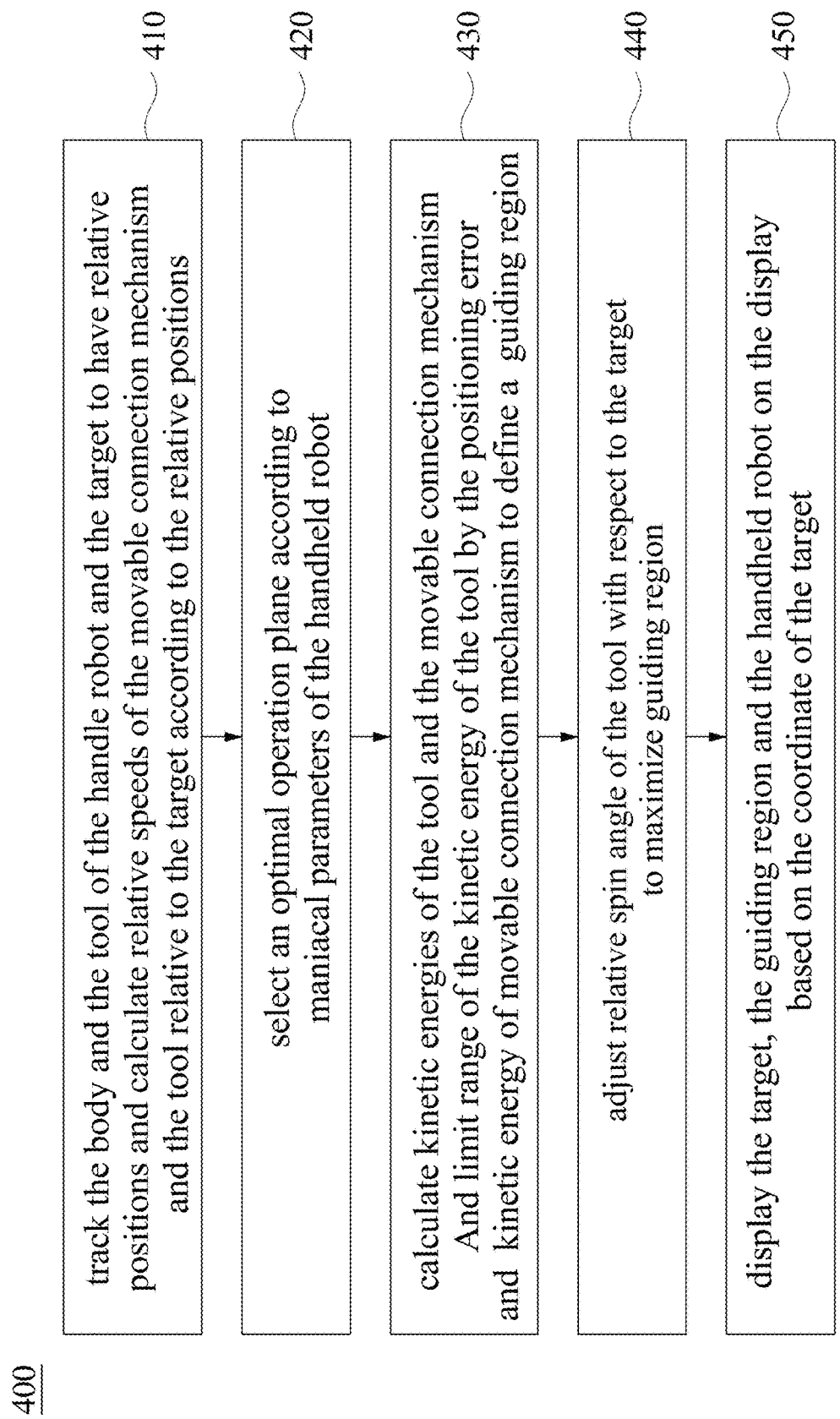
FIG. 4 illustrates a flowchart of a robot navigation method according to an embodiment of the present disclosure.

To illustrate the method of guiding the handheld robot 110 by the robot navigation system 100 and the content of the medical image and the navigation image G1 on the display 170 used to prompt the operator, please refer to FIG. 4. FIG. 4 illustrates a flowchart of a robot navigation method 400 according to an embodiment of the present disclosure. The robot navigation method 400 can be implemented by the robot navigation system 100.

As shown in FIG. 4, in this embodiment, the robot navigation method 400 includes operations 410-450 450. For the different operations of the robot navigation method 400, please refer to FIG. 5A to FIG. 8. FIGS. 5A to 8 illustrate schematic diagrams of defining a guiding region GR (as shown in FIG. 8) by a robot navigation method 400 according to an embodiment of the present disclosure.

Reference is made by FIG. 1 and FIG. 4. In operation 410, the body 120, the tool 133, and the target 300 of the handheld robot 110 are tracked by the optical tracker 140 to obtain the relative positions of the body 120, the tool 133 and the movable connection mechanism 130 with respect to the target 300. The computing module 160 calculates the speed of the movable connection mechanism 130 and the tool 133.

In this embodiment, an optical marker 151, an optical marker 152, and an optical marker 153 are located on the handheld robot 110. The optical marker 151 is located on the body 120. The optical marker 152 is located on the tool 133. The optical marker 153 is located on the target 300. Therefore, the optical tracker 140 can track the optical marker 151, the optical marker 152, and the optical marker 153 to position the body 120 and the tool 133 of the handheld robot 110 with respect to the target 300 through the optical marker 151, the optical marker 152 and the optical marker 153, respectively.

As mentioned above, the movable connection mechanism 130 is connected to the tool 133 and the body 120, and various mechanical parameters of the movable connection mechanism 130 are known. On the premise of obtaining the relative position of the body 120 with respect to the target 300, the computing module 160 can convert the relative position and speed of each movable connection mechanism 130 with respect to the target 300.

Figure 5A:
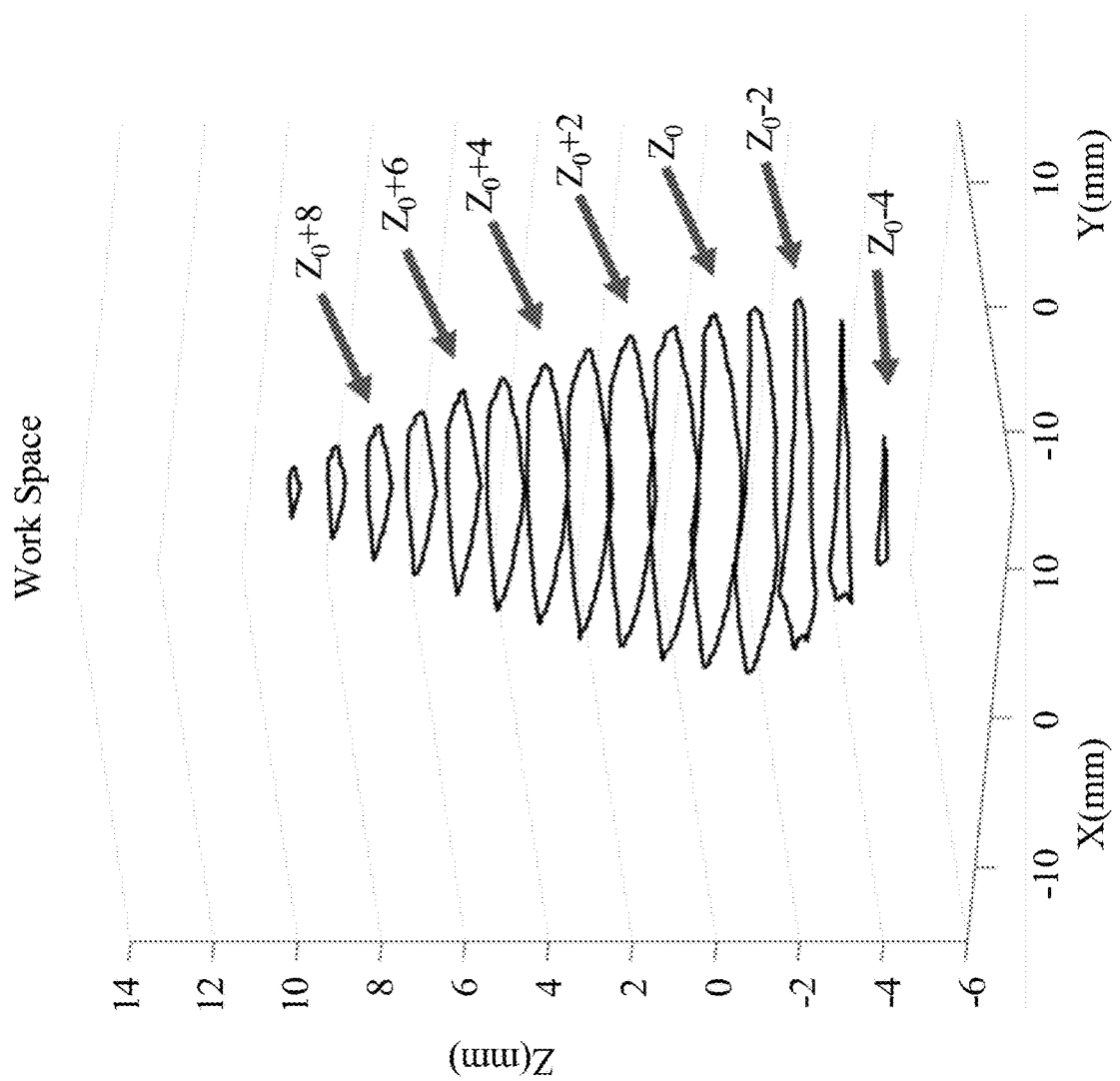
FIGS. 5A to 8 illustrate schematic diagrams of defining a guiding region by a robot navigation method according to an embodiment of the present disclosure.

Reference is made in FIG. 4 and FIG. 5A. Proceed to operation 420, The computing module 160 selects the optimal operation plane according to the mechanical parameters of the handheld robot 110. In FIG. 5A, the path P of the tip 134 of the tool 133 of the handheld robot 110 with respect to the target 300 is drawn in a three-dimensional work space.

In FIG. 5A, for the planes corresponding to different z coordinates in space (for example, $Z=z_0-4$, $z_0-2$, $z_0$, $z_0+2$, $z_0+4$, $z_0+6$, $z_0+8$), the computing module 160 can calculate the corresponding workspaces. On a specific z coordinate, the workspace of the handheld robot 110 is maximal, which means that the operator can manipulate the handheld robot within workspace range.

The boundary of the workspace range should be related to the mechanical parameters of the handheld robot 110. Specifically, the body 120 of the handheld robot 110 and the tool 133 are connected by a movable connection mechanism 130. The operator controls the movement of the body 120, and the movable connection mechanism 130 moves the tool 133 based on the body 120.

In other words, the moving range of the tool 133 is restricted by the movable connection mechanism 130. The extension of the movable connection mechanism 130 would affect the movable degree of the handheld robot 110.

Therefore, the computing module 160 selects the plane with the largest workspace as the optimal operation plane, and the operator can move the handheld robot 110 on the optimal operation plane. In this embodiment, when the z-coordinate is $z_0$, the plane corresponding to the z-coordinate of $z_0$ has the greatest dexterity range, and the plane corresponding to the z-coordinate of $z_0$ is selected as the optimal operation plane.

Figure 5B:
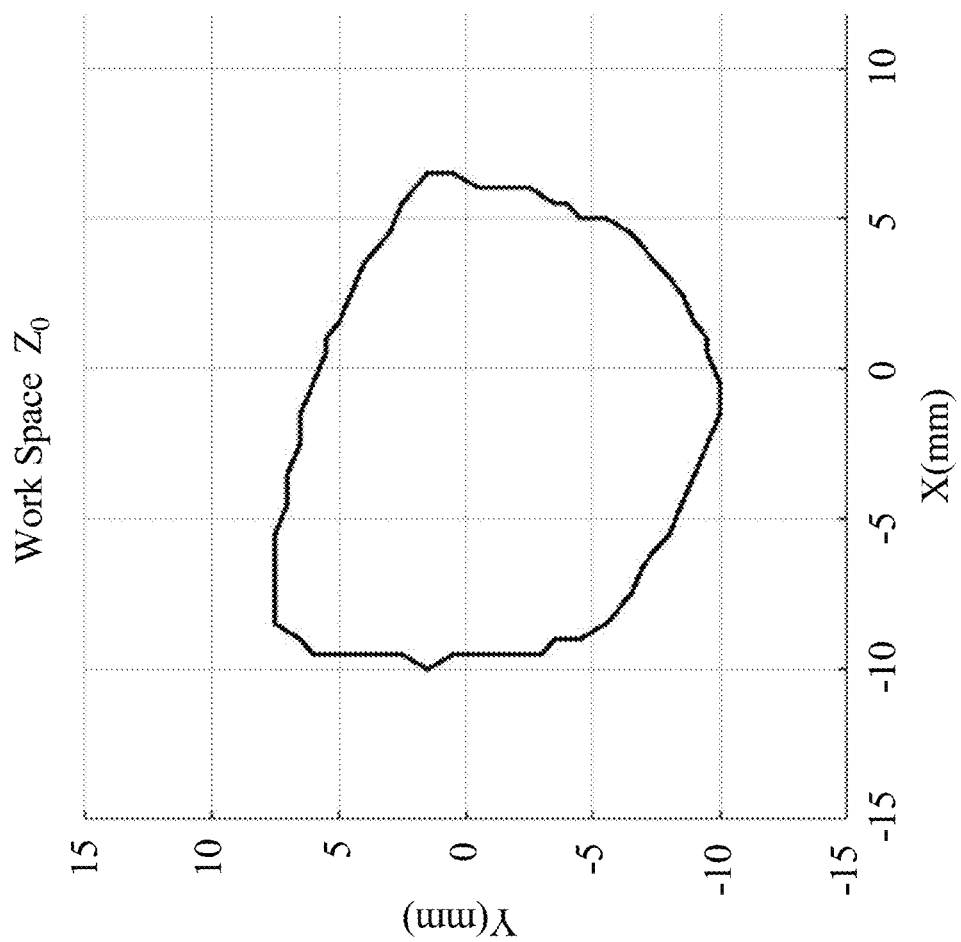

FIG. 5B illustrates the workspace range on the plane corresponding to $z_0$. When the x-coordinate, y-coordinate are closer to 0 on $z=z_0$ plane, the extension of the movable connection mechanism 130 is less, which makes the handheld robot 110 easier to move and facilitates the handheld robot 110 to approach the target 300 in different ways.

In contrast, when the x-coordinate, y-coordinate are far away from 0 on $z=z_0$ plane, the extension of the corresponding movable connection mechanism 130 is larger in order to make the tip 134 of the tool 133 to be aligned with the target 300. Therefore, the less dexterity corresponds to more difficulties to move the movable connection mechanism 130 of the handheld robot 110.

Figure 6:
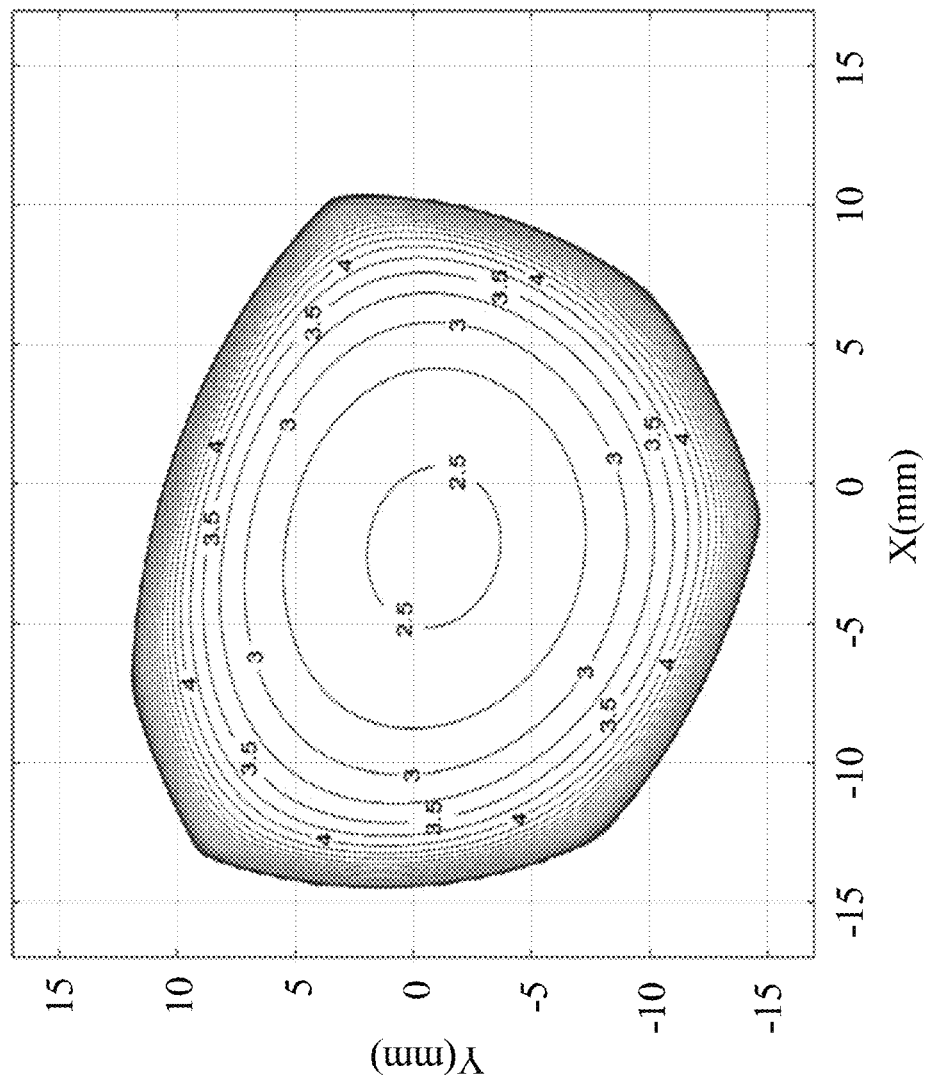

Reference is made by FIG. 4 and FIG. 6. The computing module 160 has obtained the relative positions and relative speeds of the body 120, the movable connection mechanism 130 and the tool 133 of the handheld robot 110 with respect to the target 300, and the computing module 160 has also selected optimal operation plane based on the mechanical parameters of the handheld robot 110. After the optimal operation plane is provided, proceed to operation 430 is.

In the operation 430, the computing module 160 calculates the kinetic energy of the tool 133 and limits the range of the kinetic energy of the tool 133 according to the kinetic energy from the movable connection mechanism 130 and the positioning error, thereby defining a guiding region.

In the operation 430, the guiding region is defined for the standard state of the tool 133 without deviation (for example, as shown in FIG. 2A).

For illustrative purposes, the operation 430 is described with an embodiment. In some embodiments, the operation 430 can be explained by the following inequality.

Inequality (I) is as follows:

$$\|\dot{q}\|_2 \le \|{}^B J_{ik}{}^B \mathfrak{R}\|_\infty \|\dot{h}\|_2 \le \lambda_{max}(x,y,\alpha,\beta,\gamma)\|\dot{h}\|_2 \le \lambda_{max}(x,y,\alpha,\beta,\gamma)\|K\|_\infty \|e\|_2$$

The parameter q corresponds to the position of the movable connection mechanism 130 relative to the body 120 of the handheld robot 110, and can be obtained by the controller 122 in the body 120. The parameter $\dot{q}$ represents the first derivative of the parameter q with respect to time, and corresponds to the speed of the movable connection mechanism 130.

The parameter e is the position error of the movable connection mechanism 130, which limits the maximum movable range of the movable connection mechanism 130 and the corresponding maximum achievable speed. The parameter K can convert the positioning error parameter e into a limiting parameter in speed units.

The parameter h corresponds to the path P. That is, h is the offset of the tip 134 of the tool 133 with respect to the target 300, and $\dot{h}$ represents the first derivative of the parameter h with respect to time, which corresponds to the speed of the tip 134 of the tool 133 with respect to the target 300.

The matrix ${}^B J_{ik}$ is the Jacobian matrix, and the matrix ${}^B \mathfrak{R}$ is the rotation matrix. Through matrix ${}^B J_{ik}$ and matrix ${}^B \mathfrak{R}$ coordinate conversion can be realized, so that the physical quantity under two different coordinates of parameter q and parameter h are compared under the same coordinate. In detail, the parameter q corresponds to the position of the movable connection mechanism 130 relative to the body 120 of the handheld robot 110. Therefore, the matrix ${}^B J_{ik}$ changes the parameter q to the target 300 as the reference point of the coordinates, and the matrix ${}^B \mathfrak{R}$ reflects the orientation of the movable connection mechanism 130.

As mentioned above, the relative position of the movable connection mechanism 130 with respect to the target 300 is calculated based on the body 120. Therefore, the matrix ${}^B J_{ik}$ is related to the relative position of the body 120 with respect to the target 300. Since the handle 115 held by the operator and the body 120 is fixed, the force exerted by the operator on the handheld robot 110 can be instantly reflected in the matrix ${}^B J_{ik}$.

The parameter $\lambda_{max}(x, y, \alpha, \beta, \gamma)$ corresponds to a predetermined value, which limits an upper limit of the different x-coordinates, y-coordinates for the offset orientation $\alpha$, $\beta$, $\gamma$ of the tool 133 with respect to the target 300 on the optimal operating plane (z-coordinate $z_0$) selected in the operation 420. In this embodiment, the parameter $\lambda_{max}(x, y, \alpha, \beta, \gamma)$ corresponds to the eigenvalue of the matrix ${}^B J_{ik}$ multiplied by the matrix ${}^B \mathfrak{R}$ to obtain of the matrix, which is similar to the aforementioned dexterity value, and the eigenvalue can reflect the obstructed situation of the handheld robot 110. The greater the eigenvalue of the matrix obtained by multiplying the matrix ${}^B J_{ik}$ and the matrix ${}^B \mathfrak{R}$, the more hindered the control of the movable connection mechanism 130 of the corresponding handheld robot 110 would be.

In the above inequality (I), the magnitude of the different parameter values is expressed in the mathematical form of the norm. For example, $\|\dot{q}\|$ is the size of $\dot{q}$, and $\|\dot{q}\|_2$ is the square of the size of $\dot{q}$.

The inequality (I) can be interpreted as: $\|\dot{q}\|_2$ corresponds to the kinetic energy of the movable connection mechanism 130. $\|{}^B J_{ik}{}^B \mathfrak{R}\|_\infty \|\dot{h}\|_2$ corresponds to the range of the kinetic energy $\|\dot{h}\|_2$ of the tip 134 of the tool 133, the coordinate conversion relationship between q and h is connected by ${}^B J_{ik} {}^B \mathfrak{R}$. The force applied by the operator to the body 120 through the handle 115 is included in the matrix ${}^B J_{ik}$ by the relative coordinates of the body 120 to the target 300. $\lambda_{max}(x, y, \alpha, \beta, \gamma)\|\dot{h}\|_2$ limits the upper limit of the kinetic energy $\|\dot{h}\|2$ of the tip 134 of the tool 133. $\lambda_{max}(x, y, \alpha, \beta, \gamma)\|K\|_\infty\|e\|_2$ is based on the limit of the positioning error parameter e of the movable connection mechanism 130, wherein $\lambda_{max}(x, y, \alpha, \beta, \gamma)$ is based on the limit of the kinetic energy of the tip 134 $\|\dot{h}\|_2$.

Therefore, inequality (I) corresponds to that the kinetic energy $\|\dot{h}\|2$ of the tip 134 of the tool 133 is basically greater than or equal to the kinetic energy of the movable connection mechanism 130 $\|\dot{q}\|_2$, and is also limited by the positioning error parameter e of the movable connection mechanism 130. In addition, the kinetic energy $\|\dot{h}\|2$ of the tip 134 of the tool 133 is also limited by a predetermined value $\lambda_{max}(x, y, \alpha, \beta, \gamma)$, which is reflected in the matrix ${}^B J_{ik}$ for the coordinate transformation relationship between q and h and rotation matrix ${}^B \mathfrak{R}$.

Accordingly, when the operator moves the handheld robot 110 through the handle 115, the force exerted by the operator on the handheld robot 110 would affect the relative position of the body 120 with respect to the target 300, and this will be reflected in the coordinate transformation matrix ${}^B J_{i_k}$ and matrix B$\mathfrak{R}$ on. In other words, in the inequality (I), the usable range of the matrix ${}^B J_{ik}$ and the matrix ${}^B \mathfrak{R}$ is limited, thereby limiting the movable range of the body 120 with respect to the target 300.

In summary, in the operation 430, the computing module 160 calculates the kinetic energy of the tool 133 through the matrix ${}^B J_{ik}$ for coordinate transformation relationship and the rotation matrix ${}^B \mathfrak{R}$. After coordinate conversion, the kinetic energy of the tool 133 is related to the relative position of the movable connection mechanism 130 and the tool 133 with respect to the target 300, and the range of the kinetic energy of the tool 133 is limited by the kinetic energy of the movable connection mechanism 130 and the positioning error.

FIG. 6 illustrates a contour map of the eigenvalue corresponding to different x-coordinates and y-coordinates of the matrix $^B J_{ik}$ multiplied by the matrix $^B \mathfrak{N}$ defined by the inequality (I) on the optimal operation plane determined by the operation 420. Such contour maps are also called kinetic energy maps.

In this embodiment, it is necessary to set the eigenvalue within a range of 2.5, which is an area where the handheld robot 110 can be better operated. Synthesizing the intersection of the workspace boundary in FIG. 5B and the range where the eigenvalue of FIG. 6 within 2.5 can define the guiding region. Therefore, when the handheld robot 110 moves to the guiding area, it can be better controlled by the operator. A simple guiding region and the relative relationship of the handheld robot 110 can be provided on the medical image and the navigation image G1 of the display 170, so as to achieve the effect of simply guiding the handheld robot 100.

The definition of the guiding region has been provided. Then, the range of contour lines with eigenvalue of 2.5 or less. By adjusting the spin angle of the movable connection mechanism, i.e. the γ-angle of the movable connection mechanism 130 associated with each x-coordinate, y-coordinate on $Z=z_0$ plane, FIG. 7 shows the range of contour line with specific eigenvalues can be increased so that the defined guiding region can be subsequently increased.

Figure 7:
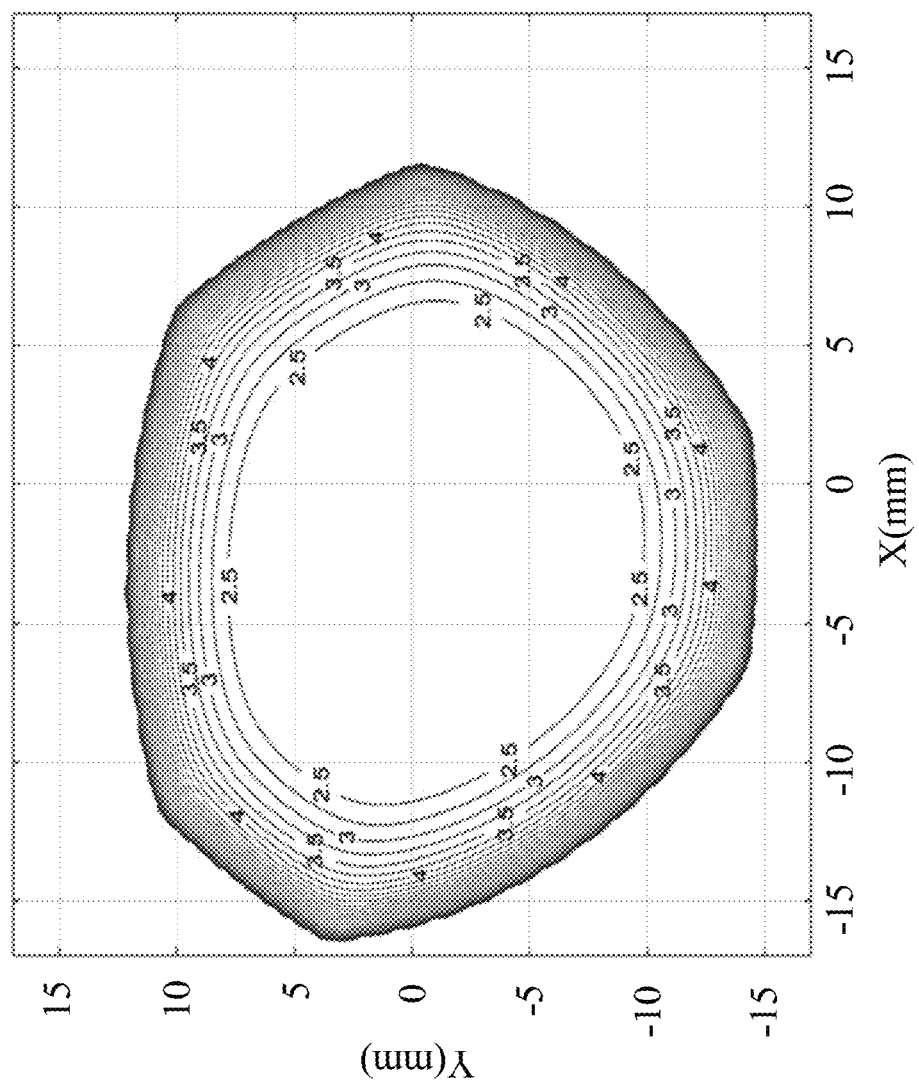
Figure 8:
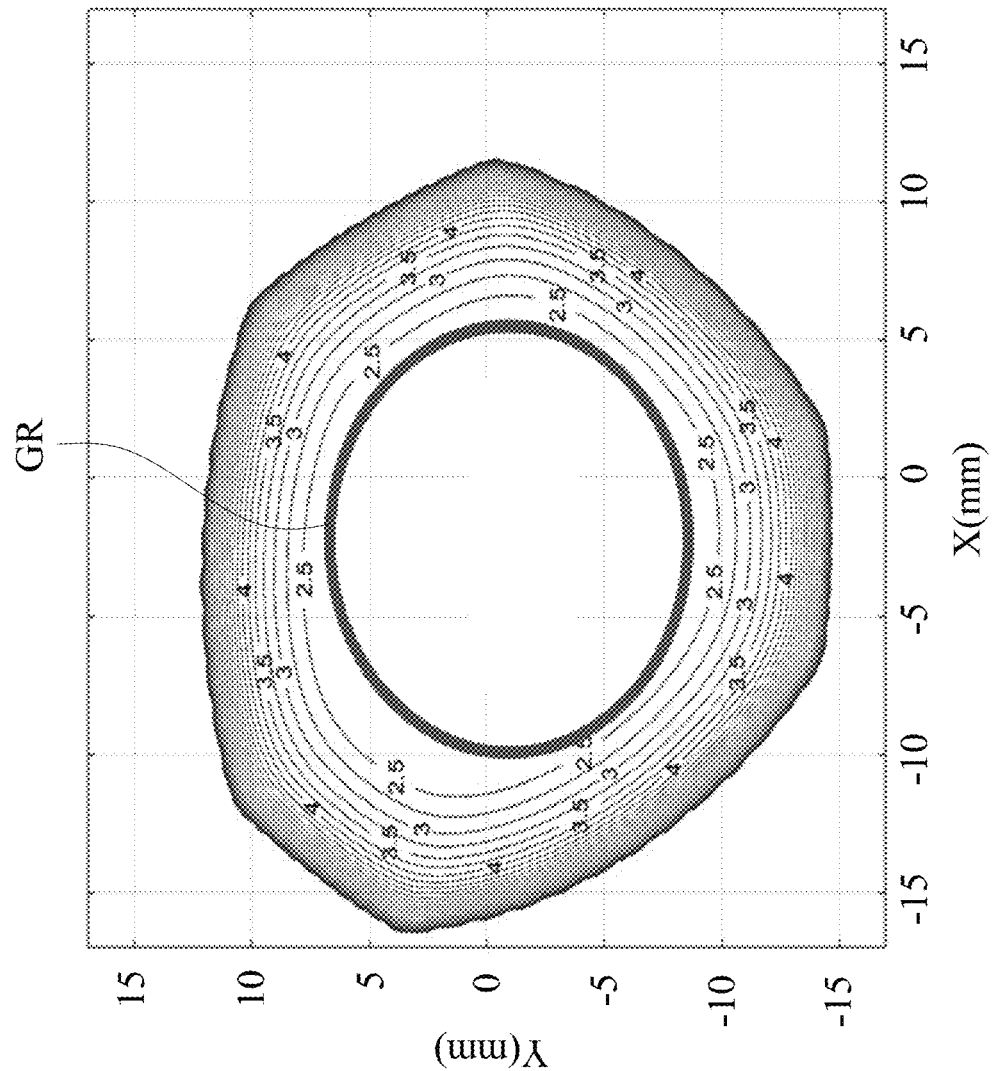

Reference is made by FIG. 4 and FIG. 7. In operation 440, By connecting the handheld robot 110 to the remote end of the computing module 160, the spin angle of the movable connection mechanism 130 (as shown in FIG. 2B) can be adjusted to maximize the guiding region. After the adjustment through the computing module 160, the range of contour lines with eigenvalue of 2.5 or less can be enlarged.

Therefore, the guiding area defined by the intersection of the contour range of the eigenvalue 2.5 or less in FIG. 7 and the dexterity range in FIG. 5B can be increased.

Continuing from FIG. 7, in FIG. 8, for the convenience of display, the circle in the intersection of the eigenvalue 2.5 contour in FIG. 7 within the workspace boundary of FIG. 5B is selected as the guiding region GR, which corresponds to that when the operator moves the handheld robot 110 into the defined guiding region GR, the remote computing module 160 can provide control signals to the transceiver 124 of the handheld robot 110, and the controller 122 would then follow the control signal received by the transceiver 124 to control the movable connection mechanism 130 in real time, so as to adjust the posture of the tool 133 in real time. The spin angle of the movable connection mechanism 130 would meet the requirements of the guiding region GR calculated by the previous computing module 160. Therefore, the guiding region GR can also be regarded as a guiding pose region.

Return to FIG. 4. In the operation 450, the target 300, the guiding region GR and the handheld robot 110 are displayed on the display 170 based on the coordinates of the target 300.

Figure 9:
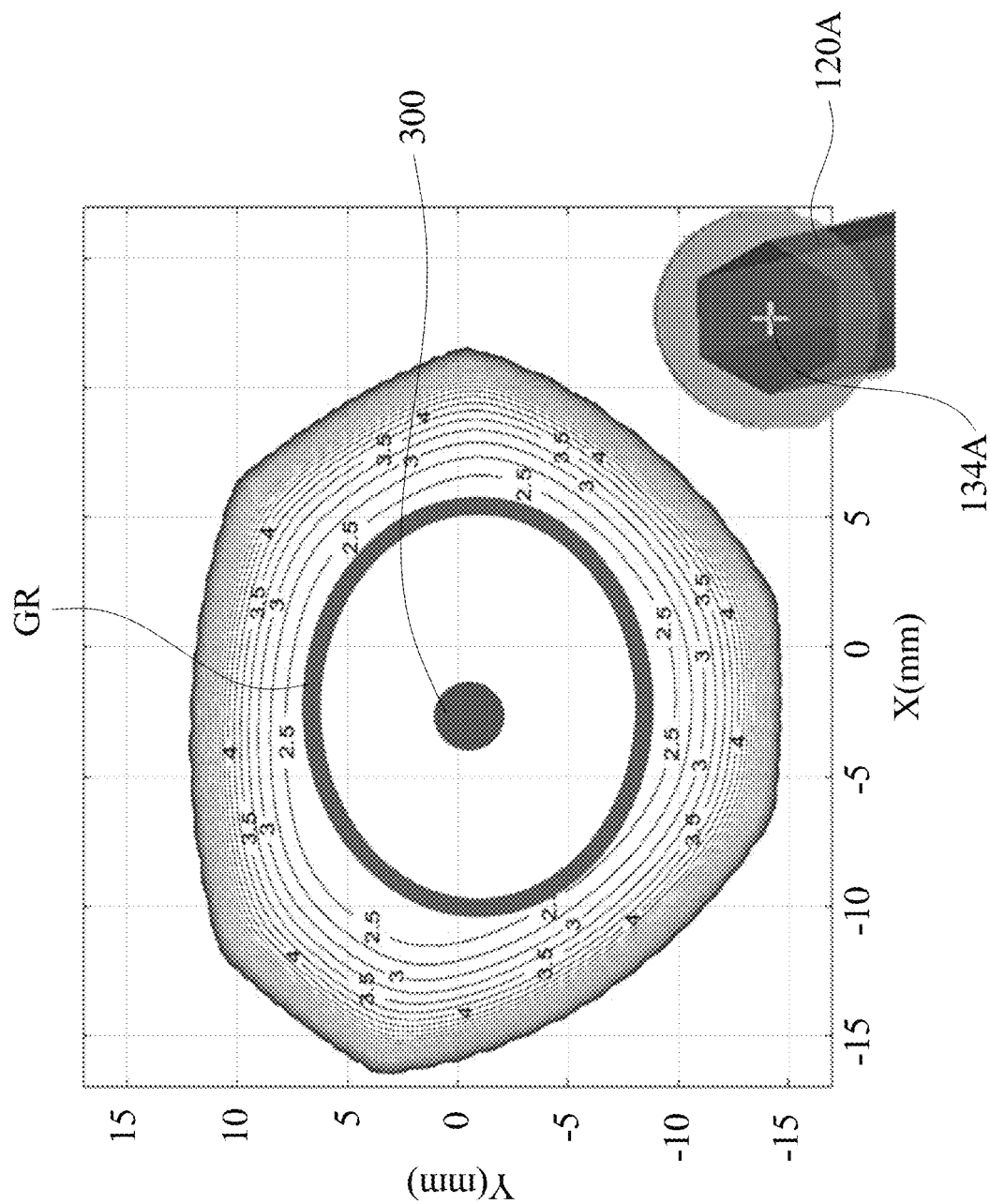
FIG. 9 illustrates a schematic view of an image provided by the robot navigation method according to an embodiment of the present disclosure.

FIG. 9 illustrates a schematic view of an image G1 provided by the robot navigation method 400 according to an embodiment of the present disclosure. For the purpose of simple description, only the navigation image part used to guide the handheld robot 110 is shown in FIG. 9. In FIG. 9, the guiding region GR and the target 300 located in the guiding region GR are marked. Subsequently, the positions of the body 120 of the handheld robot 110 and the tip 134 of the tool 133 are schematically drawn at the same time. Specifically, as shown in FIG. 9, in the medical image and the navigation image G1, the body 120 of the handheld robot 110 is schematically represented by a hexagonal cylinder 120A. The tip 134 of the tool 133 is schematically represented by a cross 134A. It should be noted that the present disclosure does not limit the representation of the body 120 or the tip 134 on the medical image and the navigation image G1. In some embodiments, the medical image and the navigation image G1 may also use other shapes to represent the body 120 and the tip 134.

Figure 10:
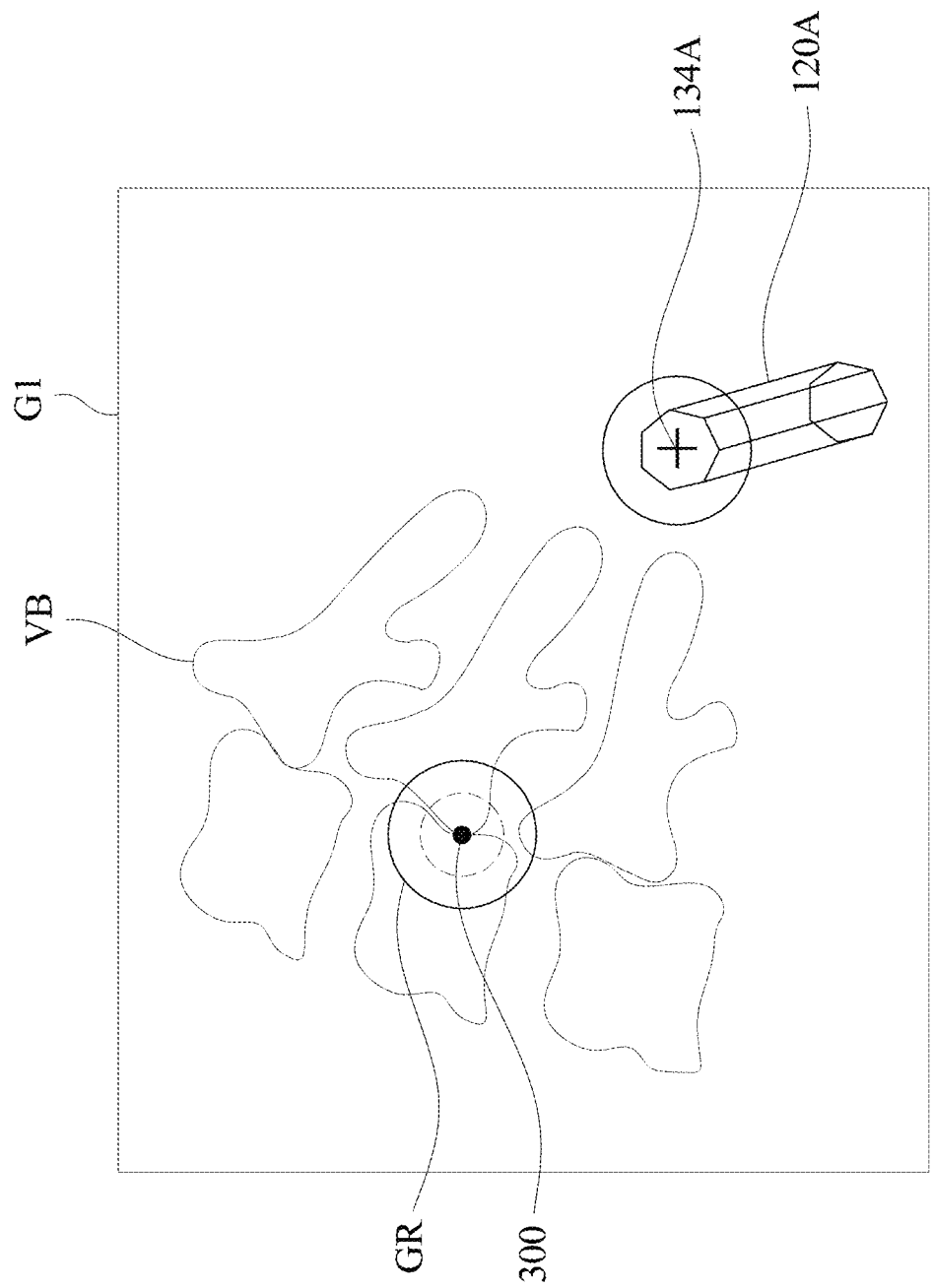
FIG. 10 illustrates a schematic view of an image provided by a robot navigation method according to an embodiment of the present disclosure.

FIG. 10 illustrates a schematic view of an image G1 provided by a robot navigation method 400 according to an embodiment of the present disclosure. The medical image and the navigation image G1 is displayed on the display 170.

The medical image and navigation image G1 shown in FIG. 10 includes a virtual object VB, a target 300, a guiding region GR and a handheld robot 110. The body 120 of the handheld robot 110 is schematically represented by a hexagonal cylinder 120A. The tip 134 of the tool 133 is schematically shown on the medical image and the navigation image G1 with a cross 134A.

In this embodiment, orthopedic surgery is taken as an example, so the virtual object VB presented on the medical image and the navigation image G1 is a bone, but it is not limited to this. In some embodiments, the virtual object VB can be drawn based on the real affected part. In some embodiments, the virtual object VB may be only for illustration, or the virtual object VB may not be shown.

Therefore, the operator can move the tip 134 close to the target in the guiding region GR according to the prompts of the medical image and the navigation image G1. In the calculation of the guiding region GR, the information of the relative position of the body 120 with respect to the target 300 has been included, and the operator only needs to use the medical image and the navigation image G1 to grasp the force of the operator on the handheld robot 110. The operator only needs to move the handheld robot 110 according to the situation presented by the medical image and the navigation image G1 and simply move the cross 134A representing the tip 134 and the hexagonal cylinder 120A corresponding to the body 120 of the handheld robot 110 in the medical image and the navigation image G1 into the guiding region GR.

In the medical image and navigation image G1 presented in FIG. 10, the area of the hexagonal cylinder 120A representing the body 120 can reflect the angle of rotation of body 120 in reality. As mentioned above, the movable connection mechanism 130 of the handheld robot 110 is limited by mechanical parameters and not all alignment methods are applicable. In this embodiment, the orientation at which the body 120 should be set can be calculated by the computing module 160. The orientation deviation of the body 120 deviates from target orientation is reflected on the medical image and the navigation image G1 as a hexagonal column 120A with an area. At this time, the tip 134 of the corresponding tool 133 cannot reach the target orientation that should be set. The operator can adjust the orientation of the body 120 with respect to the target 300 according to the prompts of the hexagonal cylinder 120A on the medical image and the navigation image G1.

For example, in some embodiments, the body 120 should be adjusted to be parallel to the vertical direction in which the target 300 is located. If the body 120 deviates from the vertical direction, the medical image and the navigation image G1 would show the projected area of the hexagonal cylinder 120A representing the body 120 due to the deviation from the vertical direction, as shown in FIG. 10. In this way, the operator can intuitively adjust the body 120 through the handle 115, so that the area of the hexagonal cylinder 120A on the medical image and the navigation image G1 of the body 120 is reduced, and the tip 134 of the corresponding tool 133 can be positioned at a suitable orientation. In other words, when the orientation error between the body 120 and the target 300 is minimized, an area of the hexagonal cylinder 120A, which is a representation corresponding to the body 120 on the medical image and the navigation image G1, would be minimized.

Figure 11:
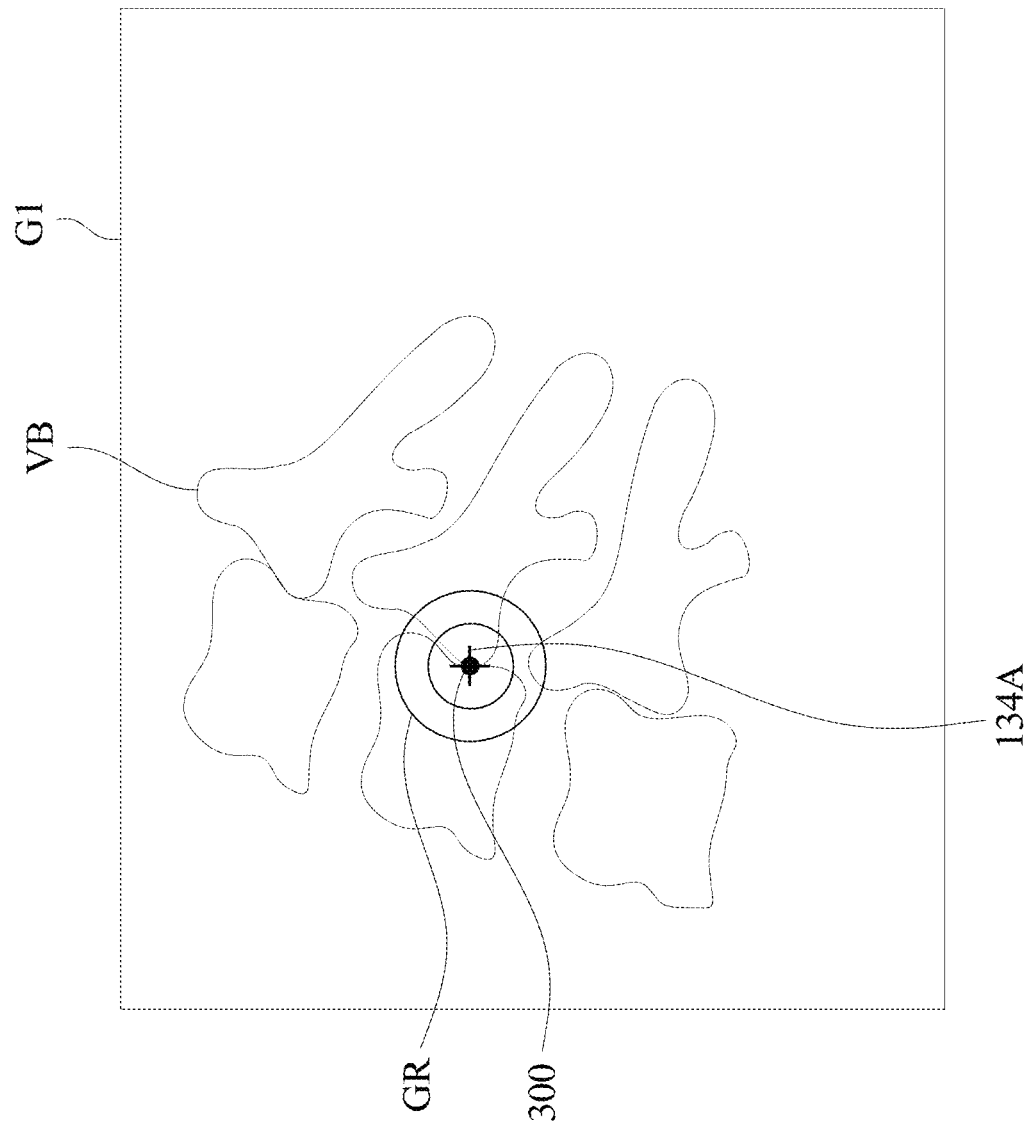
FIG. 11 continues to illustrate a schematic view of an image provided by the robot navigation method when the handheld robot in FIG. 10 is moved into place.

FIG. 11 continues to illustrate a schematic view of an image provided by the robot navigation method when the handheld robot in FIG. 10 is moved into place. As shown in FIG. 11, the cross 134A representing the tip 134 has reached the target 300, and the orientation of the body 120 is also adjusted in place, so that the tip 134 of the tool 133 can reach the orientation that should be set. Therefore, in the medical image and the navigation image G1, the area of the hexagonal cylinder 120A on the medical image and the navigation image G1 of the representative body 120 is minimized and disappears. As shown in FIG. 11, there is no hexagonal cylinder 120A representing the body 120 on the medical image and the navigation image G1.

Therefore, the medical image and the navigation image G1 shown in FIG. 11 indicate that the tool 133 corresponding to the handheld robot 110 has actually moved in place.

After the tool 133 of the handheld robot 110 is moved into position, the sight 210 of the operator can leave the display 170 to directly confirm the relative position of the tool 133 and the target 300 in reality. In some embodiments, the medical image and navigation image G1 of the display 170 can also provide medical images for the operator to confirm instantly.

Figure 12:
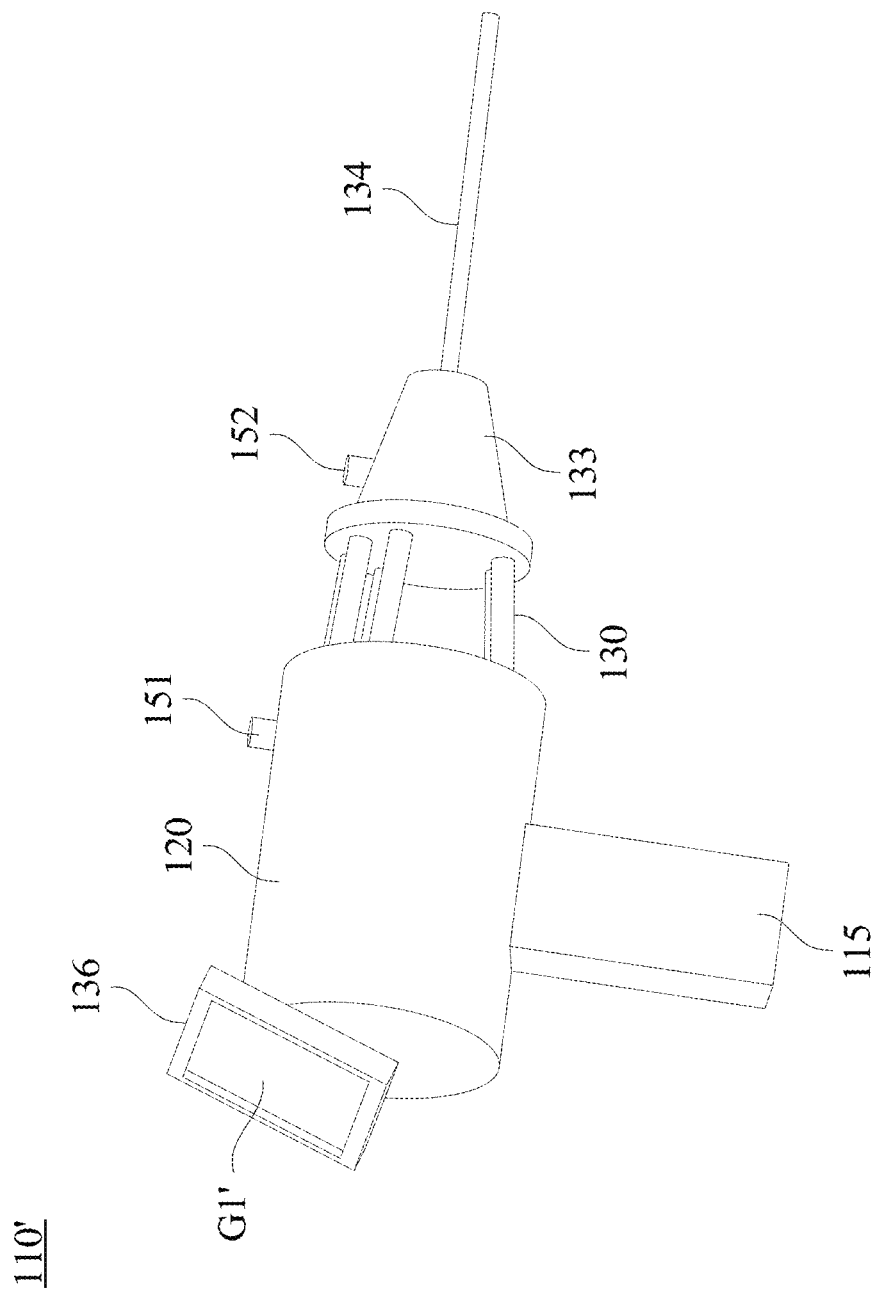
FIG. 12 illustrates a schematic view of a handheld robot according to an embodiment of the present disclosure.

FIG. 12 illustrates a schematic view of a handheld robot 110' according to an embodiment of the present disclosure. As shown in FIG. 12, in this embodiment, the handheld robot 110' includes a handle 115 for the hand 220 of the operator to hold, a body 120, a tool 133, and a movable connection mechanism 130 that connects the body 120 and the tool 133.

Similar to FIG. 1, the handheld robot 110' of FIG. 12 can be installed in the robot navigation system of the present disclosure. In order to be tracked by an optical tracker, the body 120 and the tool 133 of the handheld robot 110' are provided with optical markers 151 and 152 respectively.

The difference between the handheld robot 110' in FIG. 12 and the handheld robot 110 in FIG. 1 is that the handheld robot 110' further includes a display 136 located on the body 120. In FIG. 12, the function of the display 136 is similar to that of the display 170 shown in FIG. 1. In some embodiments, the navigation image G1' displayed on the display interface of the display 136 can be remotely provided in real time through the computing module 160 to perform the navigation function.

Figure 13:
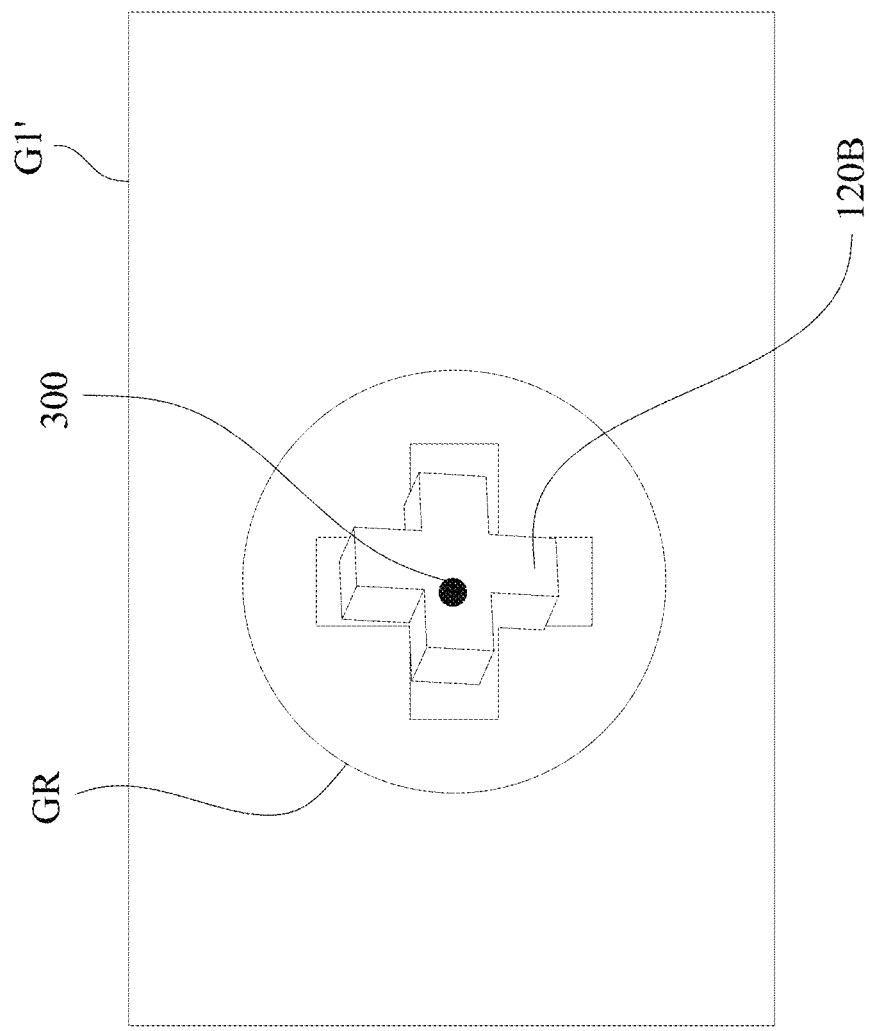
FIG. 13 is a schematic view of a navigation image provided by a robot navigation method according to an embodiment of the present disclosure.

In some embodiments, the navigation image G1' only displays the guiding area GR, the target 300, and the cross-shaped board 120B representing the body 120. In some embodiments, the navigation image G1' can also include a representative object representing the tip 134 of the tool 133, as shown in FIG. 13. FIG. 13 is a schematic view of a navigation image G1' provided by a robot navigation method according to an embodiment of the present disclosure. The operator can rotate the body 120 to align the orientation of the tool 133 to the target 300. In this embodiment, the display 136 displays the path of the cross-shaped board 120B representing the body 120 of the handheld robot 110' and the target 300. When the orientation error between the body 120 and the target 300 is minimized, the thickness of the cross-shaped plate 120B of the body on the display 136 would also be minimized.

In summary, the present disclosure provides a robot navigation system and a corresponding robot navigation method. When the operator operates the handheld robot, and there is force and reaction between the operator and the handheld robot. The robot navigation method can incorporate human influence into the control loop, and then provide images for guiding the hand-held robot to move. The image used for guidance includes a guiding region that considers relative position, relative orientation and speed between the handheld robot and the target. The operator only needs to simply move the handheld robot in the image within the guiding area, and the handheld robot corresponding to the reality is also moved in place. The overall robot navigation operation can be dynamic and intuitive. Therefore, for example, the tremor caused by the hand's involuntary motion of the operator can be suppressed by the mentioned robot navigation method.

Although the present invention has been described in considerable detail with reference to certain embodiments thereof, other embodiments are possible. Therefore, the spirit and scope of the appended claims should not be limited to the description of the embodiments contained herein. In view of the foregoing, it is intended that the present invention cover modifications and variations of this invention provided they fall within the scope of the following claims.

What is claimed is:

1. A robot navigation method, comprising:
   tracking a body, a tool and a target of a handheld robot to obtain a plurality of relative positions of the body, the tool, and a movable connection mechanism connecting the body and the tool with respect to the target;
   calculating a guiding region based on a coordinate of the target, comprising:
      calculating two relative speeds of the movable connection mechanism and the tool with respect to the target according to the relative positions;
      selecting an optimal operation plane according to mechanical parameters of the handheld robot;
      calculating the guiding region according to the relative positions and the two relative speeds of the handheld robot, wherein the guiding region is located on the optimal operation plane; and
   displaying the target, the guiding region and the handheld robot on a display based on the coordinate of the target.

2. The robot navigation method of claim 1, wherein mechanical parameters of the handheld robot comprise a position error of the movable connection mechanism, operation of calculating the guiding region based on the coordinate of the target further comprises:
   establishing a coordinate conversion relation between the movable connection mechanism and the tool;
   calculating a kinetic energy of the tool through the coordinate conversion relation, the kinetic energy is related to the two relative positions of the movable connection mechanism and the tool with respect to the target; and
   limiting a range of the kinetic energy of the tool by a kinetic energy of the movable connection mechanism and the position error, and the guiding region is defined by the range of the kinetic energy of the tool.

3. The robot navigation method of claim 1, wherein operation of calculating the guiding region based on the coordinate of the target further comprises:

adjusting a spin angle of the movable connection mechanism to maximize the guiding region displayed by the display.

4. The robot navigation method of claim 1, wherein operation of displaying the target, the guiding region and the handheld robot on the display based on the coordinate of the target further comprises:

rotating the body to minimize an orientation error of the tool with respect to the target, wherein the handheld robot displayed on the display comprises the body and the tool, and an area of a representation corresponding to the body is minimized when the orientation error is minimized.

5. The robot navigation method of claim 1, wherein operation of displaying the target, the guiding region and the handheld robot on the display based on the coordinate of the target further comprises:

rotating the body to minimize an orientation error of the tool with respect to the target, wherein the handheld robot displayed on the display comprises the body and the tool, and a thickness of a representation corresponding to the body is minimized when the orientation error is minimized.

\* \* \* \* \*